(12) United States Patent
Harris et al.

(10) Patent No.: US 9,850,192 B2
(45) Date of Patent: Dec. 26, 2017

(54) RENEWABLE ACRYLIC ACID PRODUCTION AND PRODUCTS MADE THEREFROM

(71) Applicant: Metabolix, Inc., Cambridge, MA (US)

(72) Inventors: Stephen Harris, Kennett Square, PA (US); Kevin A. Sparks, Scituate, MA (US); Oliver P. Peoples, Arlington, MA (US); Yossef Shabtai, Concord, MA (US); Christopher W. J. McChalicher, Wakefield, MA (US); Johan van Walsem, Acton, MA (US); Christopher Mirley, Winthrop, MA (US); Dirk Schweitzer, Cambridge, MA (US)

(73) Assignee: CJ Cheiljedang Corporation, Seoul (KR)

( * ) Notice: Subject to any disclaimer, the term of this patent is extended or adjusted under 35 U.S.C. 154(b) by 48 days.

(21) Appl. No.: 14/406,491

(22) PCT Filed: Jun. 7, 2013

(86) PCT No.: PCT/US2013/044671
§ 371 (c)(1),
(2) Date: Dec. 8, 2014

(87) PCT Pub. No.: WO2013/185009
PCT Pub. Date: Dec. 12, 2013

(65) Prior Publication Data
US 2015/0183708 A1    Jul. 2, 2015

Related U.S. Application Data

(60) Provisional application No. 61/657,297, filed on Jun. 8, 2012, provisional application No. 61/732,011, filed (Continued)

(51) Int. Cl.
*C07C 51/377*    (2006.01)
*C07C 67/03*    (2006.01)
(Continued)

(52) U.S. Cl.
CPC ............ *C07C 51/377* (2013.01); *A61L 15/60* (2013.01); *C07C 51/09* (2013.01); *C07C 57/04* (2013.01);
(Continued)

(58) Field of Classification Search
CPC ....... C07C 51/09; C07C 51/377; C07C 57/04; C07C 67/08; C07C 69/73; C08F 22/105;
(Continued)

(56) References Cited

U.S. PATENT DOCUMENTS 2,361,036 A    10/1944  Kung
3,720,689 A    3/1973  Pohl et al.
(Continued)

FOREIGN PATENT DOCUMENTS

CA    2 625 511 A1    3/2008
EP    2 025 760 A1    2/2009
(Continued)

OTHER PUBLICATIONS

Abate, R., et al., "Separation and Structural Characterization of Cyclic Open Chain Oligomers Produced in the Partial Pyrolysis of Microbial Poly(hydroxybutyrates)", *Macromolecules*, 28:7911-7916 (1995).
(Continued)

*Primary Examiner* — Alexander D Kim
(74) *Attorney, Agent, or Firm* — Foley Hoag LLP

(57) ABSTRACT

Processes and methods for making biobased acrylic acid products including acrylic acid, acrylic acid oligomers, acrylic acid esters, acrylic acid polymers and articles from renewable carbon resources are described herein.

27 Claims, 17 Drawing Sheets

Related U.S. Application Data on Nov. 30, 2012, provisional application No. 61/773,924, filed on Mar. 7, 2013.

(51) Int. Cl.

| | |
|---|---|
| C07C 51/09 | (2006.01) |
| C07C 57/04 | (2006.01) |
| C07C 67/08 | (2006.01) |
| C07C 69/73 | (2006.01) |
| A61L 15/60 | (2006.01) |
| C12N 15/52 | (2006.01) |
| C12P 7/62 | (2006.01) |
| C12P 7/40 | (2006.01) |
| C08F 22/10 | (2006.01) |
| C08G 63/06 | (2006.01) |
| C12P 7/42 | (2006.01) |

(52) U.S. Cl.
CPC .............. C07C 67/03 (2013.01); C07C 67/08 (2013.01); C07C 69/73 (2013.01); C08F 22/105 (2013.01); C08G 63/06 (2013.01); C12N 15/52 (2013.01); C12P 7/40 (2013.01); C12P 7/42 (2013.01); C12P 7/62 (2013.01); C12P 7/625 (2013.01); Y02E 50/343 (2013.01)

(58) Field of Classification Search
CPC .... C12P 7/42; C12P 7/62; C12P 7/625; A61L 15/60
See application file for complete search history.

(56) References Cited

U.S. PATENT DOCUMENTS

| | | |
|---|---|---|
| 4,652,685 A | 3/1987 | Cawse et al. |
| 4,851,085 A | 7/1989 | De Thomas |
| 6,117,658 A | 9/2000 | Dennis et al. |
| 6,623,730 B1 | 9/2003 | Williams et al. |
| 6,831,182 B2 | 12/2004 | Borchert et al. |
| 6,852,517 B1 | 2/2005 | Cameron et al. |
| 6,897,338 B2 | 5/2005 | Zhong et al. |
| 7,166,743 B2 | 1/2007 | Zhong et al. |
| 7,229,804 B2 | 6/2007 | Huisman et al. |
| 7,641,706 B1 | 1/2010 | McMurry et al. |
| 7,687,661 B2 | 3/2010 | Lilga et al. |
| 8,026,386 B2 | 9/2011 | Burk et al. |
| 8,048,624 B1 | 11/2011 | Lynch |
| 8,084,626 B1 | 12/2011 | Fruchey et al. |
| 8,100,990 B2 | 1/2012 | Ellens et al. |
| 8,114,643 B2 | 2/2012 | Skraly et al. |
| 8,124,388 B2 | 2/2012 | Liao et al. |
| 8,129,154 B2 | 3/2012 | Burk et al. |
| 2008/0199926 A1 | 8/2008 | Burgard et al. |
| 2009/0075351 A1 | 3/2009 | Burk et al. |
| 2009/0155866 A1 | 6/2009 | Burk et al. |
| 2009/0264672 A1 | 10/2009 | Abraham et al. |
| 2009/0325248 A1 | 12/2009 | Marx et al. |
| 2010/0145086 A1 | 6/2010 | Schrodi et al. |
| 2010/0228067 A1 | 9/2010 | Peterson et al. |
| 2010/0291644 A1 | 11/2010 | Marx et al. |
| 2010/0304453 A1 | 12/2010 | Trawick et al. |
| 2011/0045575 A1 | 2/2011 | van Dien et al. |
| 2011/0144377 A1 | 6/2011 | Eliot et al. |
| 2011/0319849 A1 | 12/2011 | Collias et al. |
| 2012/0078004 A1 | 3/2012 | Fruchey et al. |
| 2012/0129232 A1 | 5/2012 | Skraly et al. |
| 2012/0225461 A1 | 9/2012 | Dole et al. |
| 2012/0315681 A1 | 12/2012 | van Walsem et al. |
| 2013/0046075 A1 | 2/2013 | van Walsem et al. |
| 2013/0288317 A1 | 10/2013 | Ramseier et al. |
| 2014/0024769 A1 | 1/2014 | van Walsem et al. |
| 2014/0114082 A1 | 4/2014 | van Walsem et al. |
| 2014/0170714 A1 | 6/2014 | van Walsem et al. |
| 2014/0234944 A1 | 8/2014 | Zhang et al. |

FOREIGN PATENT DOCUMENTS

| | | |
|---|---|---|
| EP | 2 360 137 A1 | 8/2011 |
| JP | 3178949 A | 8/1991 |
| JP | 2002-225952 | 9/2011 |
| WO | WO 99/14313 A2 | 3/1999 |
| WO | WO 03/051813 A1 | 6/2003 |
| WO | WO 2005/095320 A1 | 10/2005 |
| WO | WO 2010/006076 A2 | 1/2010 |
| WO | WO 2010/007327 A2 | 1/2010 |
| WO | WO 2010/044112 A1 | 4/2010 |
| WO | WO 2010/092155 A1 | 8/2010 |
| WO | WO 2010/092304 A2 | 8/2010 |
| WO | WO 2011/038364 A1 | 3/2011 |
| WO | WO 2011/100601 A1 | 8/2011 |
| WO | WO 2011/100608 A1 | 8/2011 |
| WO | WO 2011/154503 A1 | 12/2011 |
| WO | WO 2012/149162 A2 | 11/2012 |
| WO | WO 2012/170793 A1 | 12/2012 |
| WO | WO 2012/170793 A8 | 12/2012 |
| WO | WO 2013/023140 A1 | 2/2013 |
| WO | WO 2013/023140 A8 | 2/2013 |
| WO | WO 2013/082264 A1 | 6/2013 |
| WO | WO 2013/142033 A1 | 9/2013 |
| WO | WO 2014/127053 A2 | 8/2014 |
| WO | WO 2014/210535 A2 | 12/2014 |

OTHER PUBLICATIONS

Abe, H., "Thermal Degradation of Environmentally Degradable Poly(hydroxyalkanoic acid)s", Macromolecular Bioscience, 6:469-486 (2006).

Alber, B., et al., "Malonyl-Coenzyme A Reductase in the Modified 3-Hydroxypropionate Cycle for Autotrophic Carbon Fixation in Archaeal *Metallosphaera* and *Sulfolobus* spp.", *Journal of Bacteriology*, 188(24):8551-8559 (2006).

Ariffin, H., et al., "Highly Selective Transformation of Poly[( R) -3-hydroxybutyric acid] into trans-Crotonic Acid by Catalytic Thermal Degradation", *Polymer Degradation and Stability*, 95:1375-1381 (2010).

Celinska, E., "Debottlenecking the 1,3-Propanediol Pathway by Metabolic Engineering", *Biotechnology Advances*, 28:519-530 (2010).

Coustou, V., et al., "A Mitochondrial NADH-dependent Fumarate Reductase Involved in the Production of Succinate Excreted by Procyclic Trypanosoma brucei", *The Journal of Biological Chemistry*, 280(17):16559-16570 (2005).

Dailly, Y., et al., "Novel Alcohol Dehydrogenase Activity in a Mutant of *Salmonella* Able to Use Ethanol as Sole Carbon Source", *FEMS Microbiology Letters*, 201:41-45 (2001).

Höfer, P., et al., "Introducing a New Bioengineered Bug. *Methylobacterium extorquens* Tuned as a Microbial Bioplastic Factory", *Landes Bioscience*, 2(2):71-79 (2011).

Kim, K.J., et al., "Effect of Metal Compounds on Thermal Degradation Behavior of Aliphatic Poly(hydroxyalkanoic acid)s", *Polymer Degradation and Stability*, 93:776-785 (2008).

Kim, K.J., et al., "Effects of Residual Metal Compounds and Chain-End Structure on Thermal Degradation of Poly(3-hydroxybutyric acid)", *Polymer Degradation and Stability*, 91:769-777 (2006).

Kim, K.J., et al., "Thermal Degradation Behavior of Poly(4-hydroxybutyric acid)", *Polymer Degradation and Stability*, 91:2333-2341 (2006).

Kockelkorn, D. and Fuchs, G., "Malonic Semialdehyde Reductase, Succinic Semialdehyde Reductase, and Succinyl-Coenzyme A Reductase from *Metallosphaera sedula*: Enzymes of the Autotrophic 3-Hydroxybutyrate Cycle in *Sulfolobales*", *Journal of Bacteriology*, 191(20): 6352-6362 (2009).

Kopinke, F.-D., et al., "Thermal Decomposition of Biodegradable Polyesters-I: Poly(β-hydroxybutryic acid)", *Polymer Degradation and Stability*, 52:25-38 (1996).

Lin, H., et al., "Increasing the Acetyl-CoA Pool in the Presence of Overexpressed Phosphoenolpyruvate Carboxylase or Pyruvate

(56) References Cited

OTHER PUBLICATIONS

Carboxylase Enhances Succinate Production in *Escherichia coli*", *Biotechnol. Prog.*, 20:1599-1604 (2004).
Lu, Z., et al., "Evolution of an *Escherichia coli* Protein with Increased Resistance to Oxidative Stress", The *Journal of Biological Chemistry*, 273(14):8308-8316 (1998).
Morikawa, H. and Marchessault, R.H., "Pyrolysis of Bacterial Polyalkanoates", *Canadian Journal of Chemistry*, 59:2306-2313 (1981).
Panagiotou, G., et al., "Overexpression of a Novel Endogenous NADH Kinase in Aspergillus nidulans Enhances Growth", *Metabolic Engineering*, 11:31-39 (2009).
Rathnasingh, C., et al., "Production of 3-Hydroxypropionic Acid via Malonyl-CoA Pathway Using Recombinant *Escherichia coli* Strains", *Journal of Biotechnology*, 157:633-640 (2012).
Sco, M.-Y., et al., "Elimination of By-Product Formation During Production of 1,3-Propanediol in Klebsiella pneumoniae by Inactivation of Glycerol Oxidative Pathway", *Applied Microbiological Biotechnology*, 84:527-534 (2009).
Song, et al., "Construction of Recombinant *Escherichia coli* Strains Producing Poly(4-hydroxybutyric acid) Homopolyester From Glucose", Database Medline (online), *U.S. National Library of Medicine*, vol. 45, No. 3:382-386 (Jun. 2005).
Tong, I.-T., et al., "1,3-Propanediol Production by *Escherichia coli* Expressing Genes from the Klebsiella pneumoniae dha Regulon", *Applied and Environmental Microbiology*, 57(12):3541-3546 (1991).
Wang, Y, et al., "Construction of Recombinant *Bacillus subtilis* for Production of Polyhydroxyalkanoates", *Applied Biochemistry and Biotechnology*, 129-132: 1015-1022 (2006).
Wolf, M., et al., "Genes Encoding Xylan and β-glucan Hydrolysing Enzymes in Bacillus subtilis: Characterization, Mapping and Construction of Strains Deficient in Lichenase, Cellulase and Xylanase", *Microbiology*, 141:281-290 (1995).
WPI database, Week 200317, Thomson Scientific, London, GB; abstract of JP 2002 255952 A Sep. 11, 2002.
Yim, H., et al., "Metabolic Engineering of *Escherichia coli* for Direct Production of 1,4-Butanediol", Nature Chemical Biology, 7(7):445-452 (2011).
Zhang, L., et al., "Microbial Production of 4-hydroxybutyrate, poly-4-hydroxybutyrate, and ply(3-hydroxybutyrate-co-4-hydroxybutyrate) by Recominant Microorganisms", Appl. Microbiol Biotechnol, 84:909-916 (2009).
Notification of Transmittal of the International Search Report and the Written Opinion of the International Searching Authority for PCT/US2011/024620, "Process for Producing a Monomer Component From a Genetically Modified Polyhydroxyalkanoate Biomass"; dated Jul. 1, 2011.
Notification Concerning Transmitall of International Preliminary Report on Patentability for PCT/US2011/024620, "Process for Producing a Monomer Component From a Genetically Modified Polyhydroxyalkanoate Biomass"; dated Aug. 23, 2012.
Notification of Transmittal of the International Search Report and the Written Opinion of the International Searching Authority for PCT/US2011/024612, "Process for Making Gamma Butyrolactone"; dated Jun. 28, 2011.
Notification Concerning Transmitall of International Preliminary Report on Patentability for PCT/US2011/024612, "Process for Making Gamma Butyrolactone"; dated Aug. 23, 2012.
Notification of Transmittal of the International Search Report and the Written Opinion of the International Searching Authority for PCT/US2012/035217, "Green Process for Producing Polyhydroxyalkanoates and Chemicals Using a Renewable Feedstock"; dated Dec. 4, 2012.
Notification Concerning Transmitall of International Preliminary Report on Patentability for PCT/US2012/035217, "Green Process for Producing Polyhydroxyalkanoates and Chemicals Using a Renewable Feedstock"; dated Nov. 7, 2013.
Notification Concerning Transmitall of International Preliminary Report on Patentability for PCT/US2012/041512, "Biorefinery Process for THF Production"; dated Dec. 27, 2013.
Notification of Transmittal of the International Search Report and the Written Opinion of The International Searching Authority for PCT/US2012/050337, "Post Process Purification for Gamma-Butyrolactone Production"; dated Dec. 4, 2012.
Kopinke, F.-D., et al., "Thermal Decomposition of Biodegradable Polyesters-I: Poly((β-hydroxybutryic acid)", *Polymer Degradation and Stability*, 52:25-38 (1996).
Lu, Z., et al., "Evolution of an *Eschcrichia coli* Protein with Increased Resistance to Oxidative Stress", The *Journal of Biological Chemistry*, 273(14):8308-8316 (1998).
Seo, M.-Y., et al., "Elimination of By-Product Formation During Production of 1,3-Propanediol in Klebsiella pneumoniae by Inactivation of Glycerol Oxidative Pathway", *Applied Microbiological Biotechnology*, 84:527-534 (2009).
Notification of Transmittal of the International Search Report and the Written Opinion of the International Searching Authority for PCT/US2012/041512, "Biorefinery Process for THF Production"; dated Oct. 16, 2012.
Notification Concerning Transmitall of International Preliminary Report on Patentability for PCT/US2012/050337, "Post Process Purification for Gamma-Butyrolactone Production"; dated Feb. 20, 2014.
Notification of Transmittal of the International Search Report and the Written Opinion of the International Searching Authority for PCT/US2013/028913, "Genetically Engineered Microorganisms for the Production of Poly-4-Hydroxybutyrate"; dated Aug. 8, 2013.
Notification Concerning Transmitall of International Preliminary Report on Patentability for PCT/US2013/028913, "Genetically Engineered Microorganisms for the Production of Poly-4-Hydroxybutyrate"; dated Oct. 2, 2014.
Notification of Transmittal of the International Search Report and the Written Opinion of the International Searching Authority for PCT/US2013/044671, "Renewable Acrylic Acid Production and Products Made Therefrom"; dated Aug. 29, 2013.
Notification Concerning Transmitall of International Preliminary Report on Patentability for PCT/US2013/044671, "Renewable Acrylic Acid Production and Products Made Therefrom"; dated Dec. 18, 2014.
Invitation to Pay Additonal Fees and Partial International Search for PCT/US2014/016122, "Process for Ultra-Pure Chemical Production From Biobased Raw Starting Materials"; dated Jul. 10, 2014.
International Search Report for PCT/US2014/016122, "Process for Ultra-Pure Chemical Production From Biobased Raw Starting Materials"; dated Nov. 13, 2014.
Invitation to Pay Additional Fees and Partial International Search for PCT/US2014/044706, "Genetically Engineered Methylotrophs for the Production of PHA Biopolymers and C3, C4, and C5 Biochemicals From Methanol or Methane as Sole Carbon Feedstock"; dated Nov. 5, 2014.
International Search Report for PCT/US2014/044706, "Genetically Engineered Methylotrophs for the Production of PHA Biopolymers and C3, C4, and C5 Biochemicals From Methanol or Methane as Sole Carbon Feedstock"; dated Feb. 2, 2015.
Notice of Allowance for U.S. Appl. No. 13/578,214, "Process for Gamma-Butyrolactone Production"; dated Feb. 2, 2015.
Notice of Allowance for U.S. Appl. No. 13/578,214, "Process for Gamma-Butyrolactone Production"; dated Dec. 11, 2014.
Non Final Office Action for U.S. Appl. No. 13/578,214, "Process for Gamma-Butyrolactone Production"; dated May 30, 2014.

RENEWABLE ACRYLIC ACID PRODUCTION AND PRODUCTS MADE THEREFROM

This application is the U.S. National Stage of International Application No. PCT/US2013/044671, filed Jun. 7, 2013, which designates the U.S., published in English, and claims the benefit of U.S. Provisional Application No. 61/657,297 filed on Jun. 8, 2012, U.S. Provisional Application No. 61/732,011 filed Nov. 30, 2012 and U.S. Provisional Application No. 61/773,924 filed on Mar. 7, 2013. The entire teachings of the above applications are incorporated herein by reference.

BACKGROUND OF THE INVENTION

With dwindling petroleum resources, fluctuating energy prices, and environmental concerns, the development of energy efficient biorefinery processes to produce biobased chemicals from renewable, low cost, carbon resources offers a unique solution to overcoming the increasing limitations of petroleum-based chemicals.

One chemical class that has many industrial uses and could be manufactured using a biorefinery process is acrylates such as acrylic acid and acrylic acid esters. The market demand for these chemicals is estimated to be nearly 4 Million Metric Tons/yr, roughly split between acrylic acid and acrylate esters. The total market size for this chemical is on the order of $11 billion/yr with annual projected growth rates of about 4%. The growth is being driven by emerging consumer markets in China and India that use acrylic acid as an intermediate in products such as personal care (diapers, hygiene pads), detergents, flocculants, polymers, coatings, adhesives and sealants.

Currently, the commercial production of petroleum-based acrylic acid is carried out via a two stage process whereby propene (a byproduct of ethylene/gasoline production) is partially oxidized in air. Renewable routes to acrylate production are also in development and include such processes as the direct production of acrylic acid from fermentation of genetically engineered microbes, production of small molecule intermediates from genetically engineered microbes such as glycerol, lactic acid, crotonic acid and 3-hydroxypropionate which are then chemically converted to acrylic acid or the production of polymeric intermediates such as polyhydroxypropionate (PHA) by genetically engineered microbes which when heated to a high temperature produce acrylic acid. The pyrolysis of biologically produced PHA polymers is a particularly advantageous route for obtaining acrylic acid and its esters as it avoids the problems of low product yield and cell toxicity associated with generating small molecule chemicals directly in the microbes. However, the process should additionally minimize the production of impurities that are generated during pyrolysis of the PHA biomass and that are recovered along with the acrylic acid.

A need therefore exists to develop biorefinery processes for manufacturing acrylic acid that address not only improvements in the yield, purity, and cost of the chemical but also uses sustainable starting materials having a more positive impact on the environment.

SUMMARY OF THE INVENTION

The invention generally relates to integrated biorefinery processes for producing a high purity, high yield, biobased, acrylic acid product(s) from renewable carbon resources, a synthetic polymer made from the biobased acrylic acid product(s) from the processes and articles made from the polymer. Processes and methods for making biobased acrylic acid products, for example, acrylic acid, acrylic acid esters, acrylic acid polymers and articles from renewable carbon resources are described herein. The processes can be a continuous or a batch process. In certain embodiments, a batch process is advantageous for producing the acrylic acid product from the biomass by subsequent processes.

In one aspect, a process for the production of an acrylic acid product from a genetically engineered microbial biomass metabolizing glucose or any other renewable feedstock to produce poly-3-hydroxypropionate (P3HP) homopolymer or copolymer inside the microbial cells, followed by controlled heating of the biomass containing P3HP homopolymer or copolymer with a catalyst forming the acrylic acid product is described. An acrylic acid product as described herein includes but is not limited to: acrylic acid, dimers of acrylic acid, trimers of acrylic acid, tetramers of acrylic acid, oligomers of acrylic acid (such as oligomers of 5 or more monomers, 10 or more monomers, 15 or more monomers), poly acrylic acid, acrylic acid esters, acrylic acid salts, acrylates, or other derivative of acrylic acid and combinations thereof.

The level of P3HP in the biomass is typically greater than 10% by weight of the total biomass. Advantages of this bioprocess include the use of a renewable carbon source as the feedstock material, production of P3HP in very high yield by the genetically engineered microbe without adverse toxicity effects to the host cell (that in some instances reduces process efficiency) and the production of biobased acrylic acid products in high yield and high purity with the use of a catalyst and/or heat.

In certain aspects, a recombinant engineered P3HP biomass from a host organism serves as a renewable source for converting 3-hydroxypropionate-containing polymer to the useful intermediate acrylic acid or acrylic acid product. In some embodiments, a source of the renewable feedstock is selected from glucose, fructose, sucrose, arabinose, maltose, lactose, xylose, ethanol, methanol, glycerol, fatty acids, vegetable oils, and biomass derived synthesis gas or a combination of two or more of these. The resultant P3HP biomass from a method of the invention is then treated in the presence of a catalyst to produce acrylic acid. In other embodiments, the P3HP biomass is washed prior to combining with the catalyst. In certain embodiments, the P3HP biomass is not washed prior to combining with the catalyst. In other embodiments, the P3HP biomass is dried prior to combining with the catalyst. In certain embodiments, the dried P3HP biomass, with or without catalyst, is combined with a processing fluid prior to heating in order to increase the efficiency of the heat transferred from an external heating source to the solid P3HP biomass thereby increasing the yield of the acrylic acid product by the prevention of unreacted polymer from forming. The processing fluid or "heat transfer fluid" can be a liquid or solid at room temperature. In certain embodiments, the process further comprises recovering the acrylic acid product and/or other volatiles (heat transfer fluids) by general methods such as condensation.

In some embodiments the acrylic acid is further processed for production of other desired commodity and specialty products, for example polyacrylic acid polymers, acrylic acid copolymers, polyacrylic acid esters, acrylic acid ester copolymers, superabsorbent materials, films, nonwoven fabrics and the like. In another embodiment, the dried P3HP biomass is mixed with excess $C_1$-$C_{12}$ alcohol and a catalyst, heated for up to 24 hours to reflux the alcohol. At the end of the reaction, an acrylic acid ester is formed and can be separated to isolate the ester for further processing. The reaction is termed a "telescopic synthesis" whereby a sequential series of chemical reactions are carried in a single reaction vessel. In this case, the first reaction is transesterification of the P3HP polymer with the alcohol forming an alkyl-3-hydroxypropionate ester followed by a dehydration reaction whereby an acrylic acid ester is finally formed. The biobased content of the final acrylic acid ester can be from about 20% to about 100% as measured by ASTM D6866 depending on whether the alcohol is petroleum-based or biobased.

The host organism used to produce the biomass containing P3HP has been genetically modified by introduction of genes and/or deletion of genes in a wild-type or genetically engineered P3HP production organism creating strains that synthesize P3HP from inexpensive renewable feedstocks. An exemplary pathway for production of P3HP is provided in US Publication No. 20120129232 A1 (incorporated by reference in its entirety) and it is understood that additional enzymatic changes that contribute to this pathway can also be introduced or suppressed for a desired production of P3HP.

In one aspect, the present invention provides a process for production of a biobased acrylic acid product. In certain embodiments of any of the aspects of the invention, acrylic acid in the product has 100% biobased carbon content (e.g., $^{14}C/C$ at least equal to $1.2 \times 10^{-12}$ as determined by $^{14}C$ isotope analysis according to ASTM D6866). In another embodiment of any of the aspects of the invention, acrylic acid in the product has greater than 90% biobased carbon content (e.g., $^{14}C/C$ at least equal to $1.2 \times 10^{-12}$ as determined by $^{14}C$ isotope analysis according to ASTM D6866).

The process of the first aspect includes combining a genetically engineered biomass comprising poly-3-hydroxypropionate, optionally a catalyst and a heat transfer fluid; heating the biomass with the catalyst to convert poly-3-hydroxypropionate to an acrylic acid product. In certain embodiments, a yield of acrylic acid product is at least 80% by weight or greater, at least 85% by weight or greater based on one gram of acrylic acid in the product per gram of the poly-3-hydroxypropionate and the amount of organic impurities present is less than 1% by weight and the biobased carbon content of the acrylic acid product is at least 90%, at least 95% or at least 98%. The genetically engineered recombinant host produces a 3-hydroxypropionate polymer.

In an embodiment of the first aspect of the invention, the genetically engineered biomass for use in the processes of the invention is from a recombinant host having a poly-3-hydroxypropionate pathway, wherein the host has a microorganism genetically engineered to produce 3-hydroxypropionic acid when provided with glucose or glycerol, wherein the microorganism converts the 3-hydroxypropionic acid to 3-hydroxypropionyl-CoA, and polymerizes the 3-hydroxypropionyl-CoA to poly-3-hydroxypropionate.

In another embodiment of the first aspect of the invention or combined with other embodiments of the invention, a recombinant host is cultured with a renewable feedstock to produce a poly-3-hydroxypropionate biomass. The produced biomass is then treated in the presence of a catalyst to produce acrylic acid product, wherein a yield of acrylic acid product(s) is at least 85% by weight, for example 86% by weight, 87% by weight, 88% by weight, 89% by weight, 90% by weight, 91% by weight, 92% by weight, 93% by weight, 94% by weight, 95% by weight, 96% by weight, 97% by weight, 98% by weight, 99% by weight, or 100% by weight.

In an embodiments of any of the aspects or combined with other embodiments of the invention, the source of the renewable feedstock is selected from glucose, fructose, sucrose, arabinose, maltose, lactose, xylose, ethanol, methanol, glycerol, fatty acids, vegetable oils, and biomass derived synthesis gas or a combination thereof.

In an embodiment of any of the aspects or combined with other embodiments of the invention, the catalyst improves the thermal stability of poly-3-hydroxypropionate and causes thermal degradation to occur 60-70° C. higher than the uncatalyzed polymer. In a further embodiment of any of the aspects, a heat transfer fluid that boils at the pyrolysis temperature, is vaporized and recovered with the acrylic acid, separated from the acrylic acid and then added back to the P3HP biomass or a heat transfer fluid which does not boil at the pyrolysis temperature but remains with the spent biomass and is recovered separately is added to the P3HP biomass prior to pyrolysis.

In a second aspect, the invention also pertains to a biobased acrylic acid product(s) produced by the processes described herein. In certain aspects, the amount of acrylic acid in the product produced is 85% or greater than 85% with total organic impurities of less than 1%.

In a third aspect, the invention pertains to a poly-3-hydroxypropionate biomass produced from renewable resources which is suitable as a feedstock for producing acrylic acid product, wherein the level of poly-3-hydroxypropionate in the biomass is greater than 30% by weight of the biomass.

In a fourth aspect, the invention pertains to a process for production of a biobased butyl acrylic acid ester product, comprising combining a genetically engineered biomass comprising poly-3-hydroxypropionate, n-butanol and a catalyst; heating the biomass with the n-butanol and catalyst to reflux for 15-24 hours; and converting the poly-3-hydroxypropionate to a butyl acrylic acid ester product having a yield of at least 80% and the biobased carbon content of the acrylic acid product is at least 40%. In certain embodiments of the fourth aspect, the catalyst for esterification of the acrylic acid is sulfuric acid, hydrochloric acid, phosphoric acid, trifluoroacetic anhydride, p-toluene sulphonic acid, methane sulfonic acid, silica, titanium dioxide, alumina or a clay, zinc oxide (ZnO), zinc chloride ($ZnCl_2$), iron chloride ($FeCl_3$), AMBERLYST™15 resin acid catalyst and dibutyl tin laurate. In certain embodiments, the n-butanol has 0% biobased content or up to and including 100% biobased content, for example, 80%, 85%, 90%, 95%, 98%, 99%. In yet other embodiments of any of the aspects or embodiments of the invention described herein, the biomass is not pyrolyzed.

In certain embodiments of any of the aspects or embodiments of the invention, the biomass host is bacteria, yeast, fungi, algae, cyanobacteria, or a mixture of any two or more thereof. The bacteria for the biomass includes but is not limited to *Escherichia coli, Alcaligenes eutrophus* (renamed as *Ralstonia eutropha*), *Bacillus* spp., *Alcaligenes latus, Azotobacter, Aeromonas, Comamonas, Pseudomonas*), *Pseudomonas, Ralstonia, Klebsiella*), *Synechococcus* sp PCC7002, *Synechococcus* sp. PCC 7942, *Synechocystis* sp. PCC 6803, and *Thermosynechococcus elongatus* BP-I (cyanobacteria), *Chlorobium tepidum* (green sulfur bacteria), *Chloroflexus auranticus* (green non-sulfur bacteria), *Chromatium tepidum* and *Chromatium vinosum* (purple sulfur bacteria), *Rhodospirillum rubrum, Rhodobacter capsulatus,* and *Rhodopseudomonas palustris*. In other embodiments, the recombinant host is algae. The algae include but are not limited to *Chlorella minutissima, Chlorella emersonii, Chlorella sorokiniana, Chlorella ellipsoidea, Chlorella* sp., or *Chlorella prototheocoides*.

In certain embodiments of the invention, poly-3-hydroxypropionate (P3HP) is chemically synthesized from 3-hydroxypropionate (3HP) monomer to a molecular weight of about 300-3×10$^6$ daltons, then heated to produce an acrylic acid product. The source of 3HP monomer can either be of biological origin produced from renewable carbon (see U.S. Pat. Nos. 7,186,541, 8,030,045 and 8,048,624), or from petroleum origin or a mixture of the two. The P3HP product generated from the chemical synthesis of 3HP is optionally mixed with catalyst and/or heat transfer fluid, then heated under an inert atmosphere to produce acrylic acid vapor which is then recovered by condensation or other methods known in the art. The biobased content of the resulting acrylic acid as determined by ASTM D6866 is therefore in the range of 0% to 100%.

In certain embodiments of the invention of any of the aspects or embodiments of the invention, the method includes heating at a temperature of about 100° C. to about 350° C. or about 200° C. to about 350° C., or from about 225° C. to 300° C. In some embodiments, the heating reduces the water content of the biomass to about 5 wt. % or less, for example, 4 weight percent or less, 3 weight % or less, 2 weight percent or less, 1 weight percent or less. In the embodiments described, the heating for example is for a time period from about 30 seconds to about 5 minutes or is from about 5 minutes to about 2 hours.

In certain embodiments the acrylic acid product obtained from any of the aspects of the invention, comprises less than 5% of undesired side products, for example, between 0.1% and about 5%, between about 0.5% and about 4%, less than about 4%, less than about 3%, less than about 2%, less than about 1%. For example, in certain methods, the presence of diacrylic acid has been linked to problems with molecular weight control, processing problems and product performance variation of acrylic polymers, thus the reduction or elimination of this side product in the acrylic acid product is desired.

In certain embodiments of any of the aspects of the invention, the catalyst in the methods for pyrolysis of the P3HP biomass of the invention is sodium hydrogen sulfate, sulfur acid or phosphoric acid. The weight percent of catalyst is in the range of about 4% to about 50%. In particular embodiments of any of the aspects, the weight % of the catalyst is in the range of about 5% to about 10%, and the heating is at 250° C.

In certain embodiments of any of the aspects of the invention, the heat transfer fluid is hexanoic acid, heptanoic acid, octanoic acid, nonanoic acid, decanoic acid, gamma-butyrolactone, THERMINOL® 50 heat transfer fluid, 50, THERMINOL® 66 heat transfer fluid, THERMINOL® 72 heat transfer fluid, THERMINOL® VP-1 heat transfer fluid, or THERMINOL® VP-3 heat transfer fluid, MARLOTHERM® SH heat transfer fluid, or MARLOTHERM® LH heat transfer fluid, THERMOFLO® A heat transfer fluid, PARATHERM® MR heat transfer fluid, or PARATHERM® OR heat transfer fluid. The heat transfer fluid can be added prior to heating and boils at the heating temperature or alternatively does not boil at the heating temperature. In certain embodiments, the heat transfer fluid remains with the biomass and can be recycled, alternatively, the heat transfer fluid is recovered from the acrylic acid product. In certain embodiments, the heat transfer fluid is a solid or a liquid at room temperature.

In certain embodiments of any of the aspects of the invention, the acrylic acid product is further recovered.

In some embodiments of any of the aspects of the invention, the catalyst is 5% by weight sodium hydrogen sulfate and the heating is at a temperature of 250° C. the heating time can be from about 30 seconds to about 2 hours.

Heating in all the embodiments and aspects of the invention is generally carried out at atmospheric pressure but can be at elevated pressures as well.

In a particular embodiment, a process is described for production of a biobased acrylic acid product, comprising combining a genetically engineered biomass comprising poly-3-hydroxypropionate and optionally a catalyst; and heating the biomass with the catalyst to convert the poly-3-hydroxypropionate to an acrylic acid product; wherein a yield of the acrylic acid product is at least 80% or 85% and the biobased carbon content of the acrylic acid product is at least 90, at least 95% or at least 98%.

Additionally in certain embodiments of any of the aspects of the invention, the expended (residual) PHA reduced biomass is further utilized for energy development, for example as a fuel to generate process steam and/or heat and the catalyst is reclaimed for further processing with P3HP biomass.

DETAILED DESCRIPTION OF THE INVENTION

Figure 1:
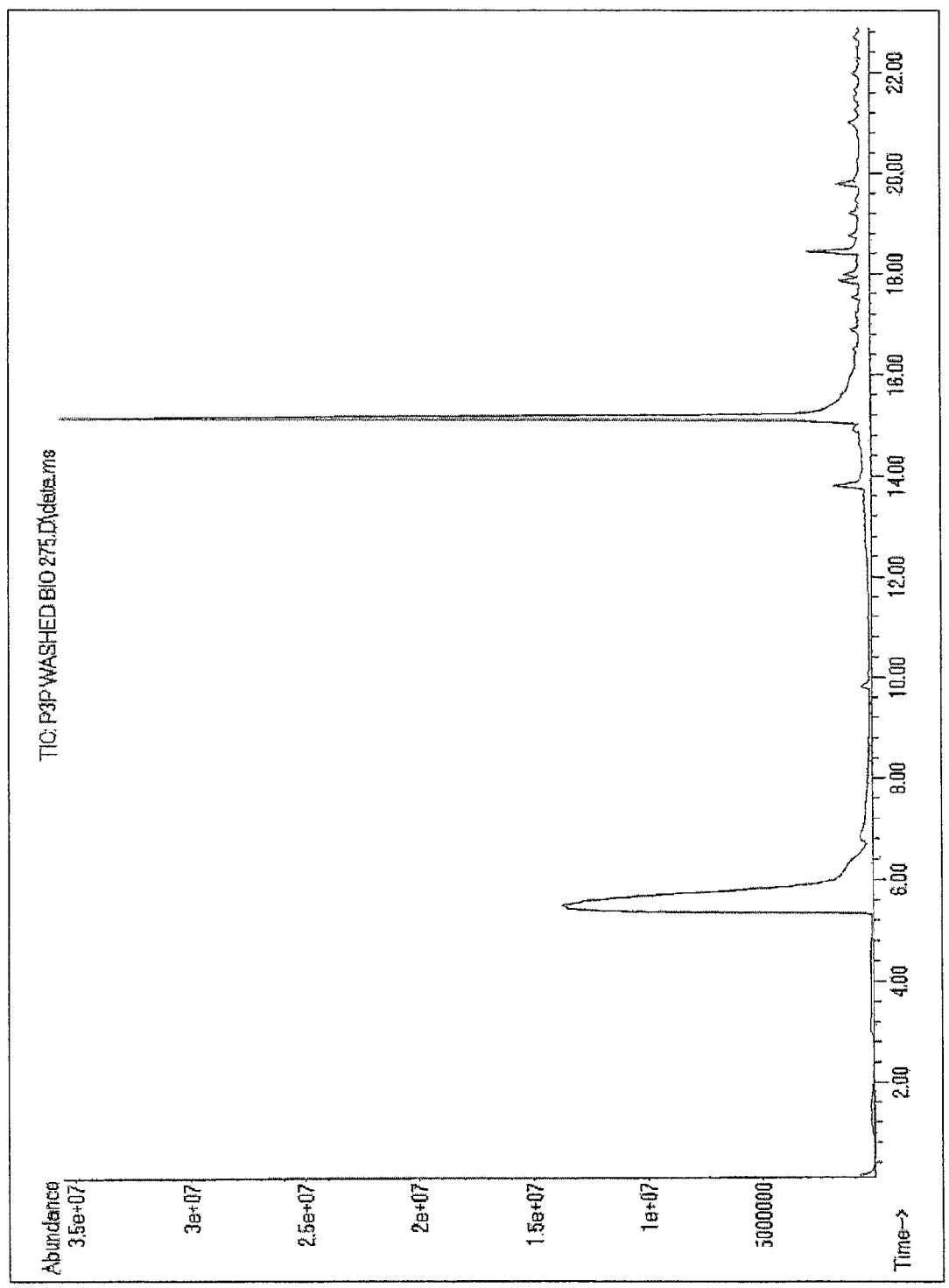
FIG. 1 is a GC-MS plot of washed-dried-ground (WDG) P3HP biomass pyrolyzed at 275° C.

A description of example embodiments of the invention follows.

The present invention provides processes and methods for the manufacture of biobased acrylic acid and acrylic acid products from genetically engineered microbes producing poly-3-hydroxypropionate polymers (P3HP biomass). Additionally, articles made by the products are also contemplated. For the purposes of this invention P3HP is defined to also include the copolymer of 3-hydroxypropionate with 3-hydroxybutyrate, 4-hydroxybutyrate, 3-hydroxyvalerate, 4-hydroxyvalerate, 5-hydroxyvalerate, 3-hydroxyhexanoate, 3-hydroxyoctanoate and lactic acid or any combination of these where the percentage of 3-hydroxypropionate in the copolymer is greater than 50%, 60%, 70%, 80%, 85%, 90% or preferably greater than 95% of the monomers in the copolymer. In certain embodiments, the P3HP biomass for production of acrylic acid products is produced using the recombinant hosts described herein. These recombinant hosts have been genetically constructed to increase the yield of P3HP by manipulating (e.g., inhibition and/or overexpression) certain genes in the P3HP pathway to increase the yield of P3HP in the biomass. The P3HP biomass is produced in a fermentation process in which the genetically engineered microbe is fed a renewable substrate. Renewable substrates include fermentation feedstocks such as sugars, vegetable oils, fatty acids, alcohols, glycerol or synthesis gas produced from plant crop materials. The level of P3HP produced in the biomass from the sugar substrate is greater than 10% (e.g., 20%, 30%, 40%, 50%, 60%, 70% or 80%) of the total dry weight of the biomass. The P3HP biomass is then combined with a catalyst and heated to thermally decompose the P3HP to biobased acrylic acid or other acrylic acid product. The following reaction shows the thermal conversion of poly-3-hydroxypropionate to acrylic acid:

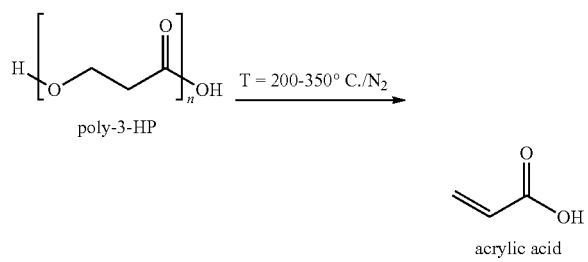

Described herein are alternative processes for manufacturing acrylic acid product(s) based on using renewable carbon sources to produce a biobased poly-3-hydroxypropionate (P3HP) polymer in a biomass that is then converted to biobased acrylic acid product(s).

Biobased, biodegradable polymers such as polyhydroxyalkanoates (PHAs), are currently produced in biomass systems, such as microbial biomass (e.g., bacteria including cyanobacteria, yeast, fungi), plant biomass, or algal biomass. Genetically-modified biomass systems have been engineered which produce a wide variety of biodegradable PHA polymers and copolymers in high yield (Lee (1996), *Biotechnology & Bioengineering* 49:1-14; Braunegg et al. (1998), *J. Biotechnology* 65:127-161; Madison, L. L. and Huisman, G. W. (1999), Metabolic Engineering of Poly-3-Hydroxyalkanoates; From DNA to Plastic, in: *Microbiol. Mol. Biol. Rev.* 63:21-53). Genetically engineered biomass systems for producing PHA's with 3-hydroxy-propionate as a monomer component have been described in U.S. Pat. Nos. 6,329,183, 6,576,450, and 8,114,643 and U.S. patent application Ser. No. 13/359,978 which are incorporated herein by reference. A good review of the biosynthesis pathways to create 3-hydroxypropionate containing polyesters is given in Andreesen et. al. (2010), *Applied and Environmental Microbiology*, August, vol. 76, No. 15, p 4919-4925.

PHA polymers are well known to be thermally unstable compounds that readily degrade when heated up to and beyond their melting points (Cornelissen et al., *Fuel*, 87, 2523, 2008). This is usually a limiting factor when processing the polymers to form products that can, however, be leveraged to create biobased, chemical manufacturing processes starting from 100% renewable resources.

When poly-3-hydroxypropionate (P3HP) is heated up to 200-350° C., it thermally degrades to volatile acrylic acid (2-propenoic acid) by random chain scission via cis-elimination (Kim et al. (2008), *Polymer Degradation and Stability*, 93:776-785). As described herein in certain embodiments, low cost catalysts are added to a genetically engineered P3HP biomass to both increase the rate of the P3HP degradation to acrylic acid and to minimize the formation of acrylic acid oligomers such as diacrylic acid which spontaneously form during production of acrylic acids (BASF technical data sheet found on the web at 2.basf.us/businesses/chemicals/acrylates/pdfs/acry-dim.pdf). The acrylic acid is recovered and the inexpensive catalyst is left with the residual biomass or can optionally be recycled back to the process after suitable regeneration including thermal regeneration. Combining the catalyst reaction with specifically genetically modified, high yielding P3HP producing biomass to produce acrylic acid is an economical and environmentally friendly alternative to the traditional petroleum-based processes.

Recombinant Hosts with Metabolic Pathways for Producing P3HP

Genetic engineering of hosts (e.g., bacteria, fungi, algae, plants and the like) as production platforms for modified and new materials provides a sustainable solution for high value industrial applications for production of chemicals. Described herein are process methods of producing monomer components and other modified chemicals from a genetically modified recombinant polyhydroxyalkanoate (PHA) biomass. The processes described herein avoid toxic effects to the host organism by producing the biobased chemical post culture or post harvesting, are cost effective and highly efficient (e.g., use less energy to make), decrease greenhouse emissions, use renewable resources and can be further processed to produce high purity chemical and polymeric products in high yield.

As used herein, "PHA biomass" is intended to mean any genetically engineered biomass that includes a non-naturally occurring amount of polyhydroxyalkanoate polymer (PHA). The wild-type PHA biomass refers to the amount of PHA that an organism typically produces in nature. In certain embodiments, the biomass titer (g/L) of PHA has been increased when compared to the host without the overexpression or inhibition of one or more genes in the PHA pathway. In certain embodiments, the PHA titer is reported as a percent dry cell weight (% wdc) or as grams of PHA/Kg biomass. In some embodiments, a source of the PHA biomass is a plant crop, bacteria, yeast, fungi, algae, cyanobacteria, or a mixture of any two or more thereof.

"Overexpression" refers to the expression of a polypeptide or protein encoded by a DNA introduced into a host cell, wherein the polypeptide or protein is either not normally present in the host cell, or where the polypeptide or protein is present in the host cell at a higher level than that normally expressed from the endogenous gene encoding the polypeptide or protein. "Inhibition" or "down regulation" refers to the suppression or deletion of a gene that encodes a polypeptide or protein. In some embodiments, inhibition means inactivating the gene that produces an enzyme in the pathway. In certain embodiments, the genes introduced are from a heterologous organism.

Genetically engineered microbial PHA production systems with fast growing organisms such as *Escherichia coli* have been developed. Genetic engineering allows for the modification of wild-type microbes to improve the production of specific PHA copolymers or to introduce the capability to produce different PHA polymers by adding PHA biosynthetic enzymes having different substrate-specificity or even kinetic properties to the natural system. Examples of these types of systems are described in Steinbuchel & Valentin, *FEMS Microbiol. Lett.* 128:219-28 (1995). PCT Publication No. WO 1998/04713 describes methods for controlling the molecular weight using genetic engineering to control the level of the PHA synthase enzyme. Commercially useful strains, including *Alcaligenes eutrophus* (renamed as *Ralstonia eutropha*), *Alcaligenes latus*, *Azotobacter vinlandii*, and *Pseudomonas*, for producing PHAs are disclosed in Lee, *Biotechnology & Bioengineering*, 49:1-14 (1996) and Braunegg et al., (1998), *J. Biotechnology* 65: 127-161. In some embodiments, a source of the biomass includes the bacteria, *E. coli*. The *E. coli* may be one which has been genetically engineered to express or overexpress one or more PHAs. Exemplary strains, fermentation, media and feed conditions are described in U.S. Pat. Nos. 6,316, 262; 6,323,010; 6,689,589; 7,081,357; 7,202,064 and 7,229, 804.

Also hosts that naturally produce PHAs can be used and further manipulated to increase PHA yields. Examples of such organisms include *Ralstonia eutropha*, *Alcaligenes latus* and *Azotobacter* but many others are well-known to those skilled in the art (Braunegg et al. 1998, *Journal of Biotechnology* 65: 127-161). The introduction of the diol dehydratase is accomplished using standard techniques as described by Peoples and Sinskey (1989, *J. Biol. Chem.* 164, 15298-15303). Genetically engineered host can then be used select for increased resistance to 3-hydroxypropionaldehyde. In other embodiments, mutations that are beneficial for the production of the P3HP homopolymers in these organisms can also be utilized. For example, specific mutations include inactivating the β-ketothiolase and/or acetoacetyl-CoA reductase genes. As these genes are generally well known and available or isolatable, gene disruptions can be readily carried out as described for example by Slater et al., 1998 (*J. Bacteriol.*) 180(8): 1979-87.

Acrylic acid, also known as 2-propenoic acid is intended to mean the carboxylic acid having the chemical formula $C_3H_4O_2$. Acrylic acid is a clear, colorless liquid that is soluble in water and is fully miscible in alcohols, ethers, and chloroform. Acrylic acid is the simplest unsaturated carboxylic acid with both a double bond and a carbonyl group. Acrylic acid includes the acrylate ion and salts. As used herein, "acrylate ester" refers to the ester form of acrylic acid. These acrylic acid forms are included herein as an acrylic acid product.

Recombinant host containing the necessary genes that will encode the enzymatic pathway for the conversion of a carbon substance to a PHA may be constructed using techniques known in the art.

The following general approach is used for generating transgenic *E. coli* PHB producers: (1) a promoterless antibiotic resistance (abr) gene is cloned in the polylinker of a suitable plasmid such as pUC18NotI or pUC18SfiI so that the major part of the polylinker is upstream of abr; (2) phb genes are subsequently cloned upstream of and in the same orientation as the abr gene; (3) the phb-abr cassette is excised as a NotI or AvrII fragment (AvrII recognizes the SfiI site in pUC18SfiI) and cloned in the corresponding sites of any plasmid like those from the pUT- or pLOF-series; (4) the resulting plasmids are maintained in *E. coli* Λ strains and electroporated or conjugated into the *E. coli* strain of choice in which these plasmids do not replicate; and (5) new strains in which the phb-abr cassette has successfully integrated in the chromosome are selected on selective medium for the host (e.g., naladixic acid when the host is naladixic acid resistant) and for the cassette (e.g., chloramphenicol, kanamycin, tetracyclin, mercury chloride, bialaphos). The resulting PHB integrants are screened on minimal medium in the presence of glucose for growth and PHB formation. Modifications of this general procedure can be made. Recombinant hosts containing the necessary genes that will encode the enzymatic pathway for the conversion of a carbon substance to PHA may be constructed using techniques well known in the art.

For example, for the production of acrylic acid monomer, a genetically engineered host that produces P3HP is needed. For the production of poly-3-hydroxypropionate, recombinant hosts such as those described in U.S. Pat. Nos. 6,329, 183, 6,576,450, 7,202,064, 8,114,643 and U.S. patent application Ser. No. 13/359,978 can be used. In general, if a host organism does not naturally produce PHA, genes for the P3HP pathway can be introduced. For example, to produce the P3HP polymers directly from carbohydrate feedstocks, a host can be further engineered to express glycerol-3-phosphate dehydrogenase and glycerol-3-phosphatase. Such recombinant *E. coli* strains and methods for their construction are known in the art (Anton, D. "Biological production of 1,3-propanediol", presented at United Engineering Foundation Metabolic Engineering II conference, Elmau, Germany, Oct. 27, 1998; PCT WO 1998/21339; Andressen et. al. (2010), *Applied and Environmental Microbiology*, August, Vol. 76, No. 15, p 4919-4925).

Suitable Host Strains

In certain embodiments, the host strain is *E. coli* K-12 strain LS5218 (Spratt et al., *J. Bacteriol.* 146 (3):1166-1169 (1981); Jenkins and Nunn, *J. Bacteriol.* 169 (1):42-52 (1987)). Other suitable *E. coli* K-12 host strains include, but are not limited to, MG1655 (Guyer et al., *Cold Spr. Harb. Symp. Quant. Biol.* 45:135-140 (1981)), WG1 and W3110 (Bachmann *Bacteriol. Rev.* 36(4):525-57 (1972)). Alternatively, *E. coli* strain W (Archer et al., *BMC Genomics* 2011, 12:9 doi:10.1186/1471-2164-12-9) or *E. coli* strain B (Delbruck and Luria, *Arch. Biochem.* 1:111-141 (1946)) and their derivatives such as REL606 (Lenski et al., *Am. Nat.* 138: 1315-1341 (1991)) are other suitable *E. coli* host strains.

Other exemplary microbial host strains include but are not limited to: *Ralstonia eutropha*, *Zoogloea ramigera*, *Allochromatium vinosum*, *Rhodococcus ruber*, *Delftia acido-* vorans, *Aeromonas caviae, Synechocystis* sp. PCC 6803, *Synechococcus elongatus* PCC 7942, *Thiocapsa pfenigii, Bacillus megaterium, Acinetobacter baumannii, Acinetobacter baylyi, Clostridium kluyveri, Methylobacterium extorquens, Nocardia corralina, Nocardia salmonicolor, Pseudomonas fluorescens, Pseudomonas oleovorans, Pseudomonas* sp. 6-19, *Pseudomonas* sp. 61-3 and *Pseudomonas putida, Rhodobacter sphaeroides, Alcaligenes latus, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor*, and *Clostridium acetobutylicum*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*.

Exemplary algal strains species include but are not limited to: *Chlorella* strains, species selected from: *Chlorella minutissima, Chlorella emersonii, Chlorella sorokiniana, Chlorella ellipsoidea, Chlorella* sp., or *Chlorella protothecoides*.

Source of Recombinant Genes

Sources of encoding nucleic acids for a P3HP pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Saccharomyces kluyveri, Clostridium kluyveri, Clostridium acetobutylicum, Clostridium beijerinckii, Clostridium saccharoperbutylacetonicum, Clostridium perjringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Chlorella minutissima, Chlorella emersonii, Chlorella sorokiniana, Chlorella ellipsoidea, Chlorella* sp., *Chlorella protothecoides, Homo sapiens, Oryctolagus cuniculus, Rhodobacter spaeroides, Thermoanaerobacter brockii, Metallosphaera sedula, Leuconostoc mesenteroides, Chloralexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salina* rum, *Geobacillus stearothermophilus, Aeropyrum pernix, Sus scrofa, Caenorhabditis elegans, Corynebacterium glutamicum, Acidaminococcusfermentans, Lactococcus lactis, Lactobacillus plantarum, Streptococcus thermophilus, Enterobacter aerogenes, Candida, Aspergillus terreus, Pedicoccus pentosaceus, Zymomonas mobilis, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum* marine gamma proteobacterium, and butyrate-producing bacterium. For example, microbial hosts (e.g., organisms) having P3HP biosynthetic production are exemplified herein with reference to an *E. coli* host. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite P3HP biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of P3HP and other compounds of the invention described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

Suitable Strategies and Expression Control Sequences for Recombinant Gene Expression Strategies for achieving expression of recombinant genes in *E. coli* have been extensively described in the literature (Gross, Chimica Oggi 7(3):21-29 (1989); Olins and Lee, Cur. Op. Biotech. 4:520-525 (1993); Makrides, Microbiol. Rev. 60(3):512-538 (1996); Hannig and Makrides, Trends in Biotech. 16:54-60 (1998)). Expression control sequences can include constitutive and inducible promoters, transcription enhancers, transcription terminators, and the like which are well known in the art. Suitable promoters include, but are not limited to, $P_{lac}$, $P_{tac}$, $P_{trc}$, $P_R$, $P_L$, $P_{trp}$, $P_{phoA}$, $P_{ara}$, $P_{uspA}$, $P_{rspU}$, $P_{syn}$ (Rosenberg and Court, Ann. Rev. Genet. 13:319-353 (1979); Hawley and McClure, Nucl. Acids Res. 11 (8):2237-2255 (1983); Harley and Raynolds, Nucl. Acids Res. 15:2343-2361 (1987); also ecocyc.org and partsregistry.org.

Construction of Recombinant Hosts

Recombinant hosts containing the necessary genes that will encode the enzymatic pathway for the conversion of a carbon substrate to P3HP may be constructed using techniques well known in the art.

Methods of obtaining desired genes from a source organism (host) are common and well known in the art of molecular biology. Such methods can be found described in, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999). For example, if the sequence of the gene is known, the DNA may be amplified from genomic DNA using polymerase chain reaction (Mullis, U.S. Pat. No. 4,683,202) with primers specific to the gene of interest to obtain amounts of DNA suitable for ligation into appropriate vectors. Alternatively, the gene of interest may be chemically synthesized de novo in order to take into consideration the codon bias of the host organism to enhance heterologous protein expression. Expression control sequences such as promoters and transcription terminators can be attached to a gene of interest via polymerase chain reaction using engineered primers containing such sequences. Another way is to introduce the isolated gene into a vector already containing the necessary control sequences in the proper order by restriction endonuclease digestion and ligation. One example of this latter approach is the BioBrick™ technology (see the world wide web at biobricks.org) where multiple pieces of DNA can be sequentially assembled together in a standardized way by using the same two restriction sites.

In addition to using vectors, genes that are necessary for the enzymatic conversion of a carbon substrate to P3HP can be introduced into a host organism by integration into the chromosome using either a targeted or random approach. For targeted integration into a specific site on the chromosome, the method generally known as Red/ET recombineering is used as originally described by Datsenko and Wanner (*Proc. Natl. Acad. Sci. USA*, 2000, 97, 6640-6645). Random integration into the chromosome involved using a mini-Tn5 transposon-mediated approach as described by Huisman et al. (U.S. Pat. Nos. 6,316,262 and 6,593,116).

Culturing of Host to Produce P3HP Biomass

In general, the recombinant host is cultured in a medium with a carbon source and other essential nutrients to produce the P3HP biomass by fermentation techniques either in batches or continuously using methods known in the art. Additional additives can also be included, for example, Vitamin B12, antifoaming agents and the like for achieving desired growth conditions. Fermentation is particularly useful for large scale production of P3HP polymer. An exemplary method uses bioreactors for culturing and processing the fermentation broth to the desired product. Other processes such as separation techniques can be combined with fermentation for large scale and/or continuous production of the P3HP polymer free of the biomass.

As used herein, the term "feedstock" refers to a substance used as a carbon raw material in an industrial process. When used in reference to a culture of organisms such as microbial or algae organisms such as a fermentation process with cells, the term refers to the raw material used to supply a carbon or other energy source for the cells. Carbon sources useful for the production of acrylic acid from P3HP biomass include simple, inexpensive sources, for example, glucose, sucrose, lactose, fructose, xylose, maltose, arabinose, ethanol, methanol, glycerol and the like alone or in combination. In other embodiments, the feedstock is molasses or starch, fatty acids, vegetable oils or a lignocelluloses material and the like. It is also possible to use organisms to produce the P3HP biomass that grow on synthesis gas ($CO_2$, CO and hydrogen) produced from renewable biomass resources.

Introduction of P3HP pathway genes allows for flexibility in utilizing readily available and inexpensive feedstocks. A "renewable" feedstock refers to a renewable energy source such as material derived from living organisms or their metabolic byproducts including material derived from biomass, often consisting of underutilized components like chaff or stover. Agricultural products specifically grown for use as renewable feedstocks include, for example, corn, soybeans, switchgrass and trees such as poplar, wheat, flaxseed and rapeseed, sugar cane and palm oil. As renewable sources of energy and raw materials, agricultural feedstocks based on crops are the ultimate replacement of declining oil reserves. Plants use solar energy and carbon dioxide fixation to make thousands of complex and functional biochemicals beyond the current capability of modern synthetic chemistry. These include fine and bulk chemicals, pharmaceuticals, nutraceuticals, flavanoids, vitamins, perfumes, polymers, resins, oils, food additives, bio-colorants, adhesives, solvents, and lubricants.

Combining P3HP Biomass with Pyrolysis Catalyst

In general, during or following production (e.g., culturing) of the P3HP biomass, the biomass is optionally combined with a catalyst under suitable conditions to help convert the P3HP polymer to a high purity acrylic acid product e g minimizing the formation of diacrylic acid or higher molecular weight acrylic acid oligomers during pyrolysis of the biomass. The catalyst (in solid or solution form) and biomass are combined for example by mixing, flocculation, centrifuging or spray drying, or other suitable method known in the art for promoting the interaction of the biomass and catalyst driving an efficient and specific conversion of P3HP to acrylic acid. In some embodiments, the biomass is initially washed and then dried prior to combining with the catalyst. The dried biomass is then re-suspended in water prior to combination with the catalyst. In other embodiments the biomass is not washed prior to combining with the catalyst whereby the catalyst is added to the biomass directly after fermentation and then the biomass+catalyst is dried. The drying step can be carried out for example at a temperature between about 100° C. and about 150° C. and for an amount of time to reduce the water content of the biomass to less than about 5% weight dry biomass. Suitable temperatures and duration for drying are determined for product purity and yield and can in some embodiments include low temperatures for removing water (such as between 25° C. and 150° C.) for an extended period of time or in other embodiments can include drying at a high temperature (e.g., above 450° C.) for a short duration of time. Under "suitable conditions" refers to conditions that suppress the formation of diacrylic acid or higher molecular weight acrylic acid oligomers. For example, under conditions that maximize the generation of the product acrylic acid such as in the presence of co-agents or other materials that contributes to the reaction yield.

As used herein, "pyrolysis catalyst" refers to a substance that initiates or accelerates a chemical reaction without itself being affected or consumed in the reaction and that inhibits the formation of unwanted impurities or chemical compounds during pyrolysis or other chemical reactions involving the P3HP biomass. Examples of useful pyrolysis catalysts for the production of biobased acrylic acid from P3HP include Bronstead-Lowry acids or protic acids that have low volatility or are nonvolatile (e.g. nonvolatile at T≥200° C.); alkali, alkali earth or amine salts of these acids are useful as well as mixtures of any of these catalysts that are soluble in water up to 90% by weight. In certain embodiments, the catalyst decreases the temperature at which initiation of the thermal decomposition of the P3HP polymer occurs and increases the rate of thermal decomposition at certain pyrolysis temperatures (e.g., about 200° C. to about 350° C.). Examples of suitable catalysts include $H_2SO_4$, $H_3PO_4$ or $H_3BO_3$ $NaHSO_4$, $(NH_4)_2SO_4$, $ZnSO_4$, $CuSO_4$, $KHSO_4$, $(NH_4)_3PO_4 \cdot H_2O$, $NH_4NO_3$ and $AlCl_3$.

In certain embodiments, the amount of pyrolysis catalyst is about 0.1% to about 15% or about 1% to about 25%, or 4% to about 50%, or about 4% to about 50% based on the weight of catalyst relative to the dry solid weight of the biomass. In some embodiments, the amount of catalyst is between about 7.5% and about 12%. In other embodiments, the amount of catalyst is about 0.5% dry cell weight, about 1%, about 2%, about 3%, about 4%, about 5, about 6%, about 7%, about 8%, about 9%, or about 10%, or about 11%, or about 12%, or about 13%, or about 14%, or about 15%, or about 20%, or about 30%, or about 40% or about 50% or amounts in between these.

As used herein, the term "sufficient amount" when used in reference to a chemical reagent in a reaction is intended to mean a quantity of the reference reagent that can meet the demands of the chemical reaction and the desired purity of the product.

Thermal Degradation of the P3HP Biomass

"Heating," "pyrolysis", "thermolysis" and "torrefying" as used herein refer to thermal degradation (e.g., decomposition) of the P3HP biomass for conversion to acrylic acid. In general, the thermal degradation of the P3HP biomass occurs at an elevated temperature optionally in the presence of a catalyst which is added to minimize or eliminate the formation of diacrylic acid or higher molecular weight acrylic acid oligomers as well as increase the rate at which thermal degradation occurs. Additionally, a processing fluid can be optionally combined with the P3HP biomass prior to heating in order to increase the efficiency of the heat transferred from an external heating source to the solid P3HP biomass and to prevent unreacted polymer from forming which increases the overall acrylic acid yield. As defined herein, "processing fluid" or "heat transfer fluid" refers to an inert liquid or solid (at room temperature) which is added to wet or dry P3HP biomass in order to aid heat flow within the biomass during pyrolysis facilitating the formation of acrylic acid vapor.

In certain embodiments, the heating temperature for the processes described herein is between about 200° C. to about 400° C. In some embodiments, the heating temperature is about 200° C. to about 350° C. In other embodiments, the heating temperature is about 300° C. "Pyrolysis" typically refers to a thermochemical decomposition of the biomass at elevated temperatures over a period of time. The duration can range from a few seconds to hours. In certain conditions, pyrolysis occurs in the absence of oxygen or in the presence of a limited amount of oxygen to avoid oxygenation. The processes for P3HP biomass pyrolysis can include direct heat transfer or indirect heat transfer. They may also include the use of a heat transfer fluid. The purpose of the heat transfer fluid is to rapidly and efficiently transfer heat energy from the heating source to the solid P3HP biomass and to prevent undegraded or partially degraded P3HP from forming during pyrolysis. This is accomplished through a complex combination of conductive and convective heat transfer whereby the fluid is in intimate contact with both the heat source and the P3HP biomass. The desired properties of the heat transfer fluid include high heat capacity, low viscosity, low vapor pressure, nonflammable, nontoxic, low cost and high thermal and oxidative stability at the temperature of use. The term heat transfer fluid as used herein refers also to materials known as process fluids, hot oils, cutting fluids, thermal fluids or thermicals.

Another method of heating the P3HP biomass to release acrylic acid is called "Flash pyrolysis" which refers to quickly heating the biomass at a high temperature for fast decomposition of the P3HP biomass, for example, depolymerization of a P3HP in the biomass. An example of flash pyrolysis is RTP™ rapid thermal pyrolysis. RTP™ technology and equipment from Envergent Technologies, Des Plaines, Ill. converts feedstocks into bio-oil. "Torrefying" refers to the process of torrefaction, which is an art-recognized term that refers to the drying of biomass at elevated temperature with loss of water and organic volatiles to produce a torrefied biomass with enhanced solid fuel properties. The torrefied biomass typically has higher heating value, greater bulk density, improved grindability for pulverized fuel boilers, increased mold resistance and reduced moisture sensitivity compared to biomass dried to remove free water only (e.g. conventional oven drying at 105° C.). The torrefaction process typically involves heating a biomass in a temperature range from 200-350° C., over a relatively long duration (e.g., 10-30 minutes), typically in the absence of oxygen. The process results for example, in a torrefied biomass having a water content that is less than 7 wt % of the biomass. The torrefied biomass may then be processed further. In some embodiments, the heating is done in a vacuum, at atmospheric pressure or under controlled pressure. In certain embodiments, the heating is accomplished without the use or with a reduced use of petroleum generated energy.

In certain embodiments, the P3HP biomass is dried prior to heating. Alternatively, in other embodiments, drying is done during the thermal degradation (e.g., heating, pyrolysis or torrefaction) of the P3HP biomass. Drying reduces the water content of the biomass. In certain embodiments, the biomass is dried at a temperature of between about 100° C. to about 350° C., for example, between about 200° C. and about 275° C. In some embodiments, the dried P3HP biomass has a water content of 5 wt %, or less.

In certain embodiments, a heat transfer fluid is combined with the P3HP biomass or the P3HP biomass/catalyst mixture prior to heating. The wt % heat transfer fluid can be 10%, 20%, 3%, 40%, 50%, 60%, 70%, 80%, 90% or 100% based on the weight of the P3HP biomass. The P3HP biomass can also be suspended in the heat transfer fluid where the weight % P3HP biomass is 50%, 40%, 30%, 20%, 10%, 5% or 1% by weight of the fluid. In another embodiment, the heat transfer fluid boils off at the temperature at which the P3HP biomass is heated and is recovered along with the acrylic acid produced. Examples of these type of heat transfer fluids include fatty acids such as hexanoic acid, heptanoic acid, octanoic acid, nonanoic acid and decanoic acid, also gamma-butyrolactone (GBL), diphenyl oxide/biphenyl ethers such as THERMINOL® VP-1 synthetic heat transfer fluid and THERMINOL® VP-3 synthetic heat transfer fluid (Solutia Inc.). In a further embodiment, the heat transfer fluid does not boil at the temperature at which the P3HP biomass is heated to produce acrylic acid varpor but rather remains with the spent biomass after the P3HP is completely converted to acrylic acid. Examples of these include THERMINOL® 50 heat transfer fluid, THERMINOL® 59 heat transfer fluid, THERMINOL® 66 heat transfer fluid and THERMINOL® 72 heat transfer fluid (Solutia Inc.), MARLOTHERM® SH heat transfer fluid or MARLOTHERM® LH (Sasol), THERMOFLOW® A heat transfer fluid (Chem Group), PARATHERM® MR heat transfer fluid or PARATHERM® OR heat transfer fluid (Paratherm Corp.) and DOWTHERM® heat transfer fluid (Dow).

In certain embodiments, the heating of the P3HP biomass/catalyst mixture is carried out for a sufficient time to efficiently and specifically convert the P3HP biomass to acrylic acid. In certain embodiments, the time period for heating is from about 30 seconds to about 1 minute, from about 30 seconds to about 1.5 minutes, from about 1 minute to about 10 minutes, from about 1 minute to about 5 minutes or a time between, for example, about 1 minute, about 2 minutes, about 1.5 minutes, about 2.5 minutes, about 3.5 minutes.

In other embodiments, the time period is from about 1 minute to about 2 minutes. In still other embodiments, the heating time duration is for a time between about 5 minutes and about 30 minutes, between about 30 minutes and about 2 hours, or between about 2 hours and about 10 hours or for greater that 10 hours (e.g., 24 hours).

In certain embodiments, the heating temperature is at a temperature of about 200° C. to about 350° C. including a temperature between, for example, about 205° C., about 210° C., about 215° C., about 220° C., about 225° C., about 230° C., about 235° C., about 240° C., about 245° C., about 250° C., about 255° C. about 260° C., about 270° C., about 275° C., about 280° C., about 290° C., about 300° C., about 310° C., about 320° C., about 330° C., about 340° C., or 345° C. In certain embodiments, the temperature is about 250° C. In certain embodiments, the temperature is about 275° C. In other embodiments, the temperature is about 300° C.

In certain embodiments, "recovering" the acrylic acid vapor and/or the heat transfer fluid includes condensing the vapor generated during pyrolysis of the biomass. As used herein, the term "acrylic acid vapors" includes the components acrylic acid, acetic acid, diacrylic acid, biomass-generated fatty acids, water, heat transfer fluids and any other by-products produced during pyrolysis of the P3HP biomass. As used herein, the term "recovering" as it applies to the vapor means to isolate it from the P3HP biomass materials, for example including but not limited to: recovering by fractional condensation, separation methodologies, such as the use of membranes, gas (e.g., vapor) phase separation, such as distillation, and the like. Thus, the recovering may be accomplished via a fractional condensation mechanism that captures the pyrolysis vapor, condenses the acrylic acid and any other condensable compounds in the vapor to a liquid form, separates the acrylic acid it from the lower and higher boiling condensable components and transfers all of the components away from the biomass materials.

The operation of a fractional condenser for separation of acrylic acid has been described in U.S. Pat. No. 6,646,161. In general, the hot acrylic acid vapor from the pyrolysis reactor enters the bottom of the fractional condensation column after being cooled to 100-180° C. using a heat exchanger. The column contains separatory internals such as bubble trays, sieve trays, valve trays or dual-flow trays for the fractional condensation of the hot vapor mixture produced by the thermolysis reactor. The acrylic acid vapor is then allowed to ascend the column interacting with the separatory internals and separating into low, medium and high boiling fractions. To effect the separation there are multiple cooling devices which can be located at the top, middle and bottom portions of the column. The condensed fractions from the hot vapor mixture are removed by side take-offs from different sections of the column depending on if the liquids are low boilers (near the column top), medium boilers (middle section of column) or high boilers a.k.a heavies (lower section of column). Crude acrylic acid can be removed as an intermediate boiling fraction via an installed collection tray in the middle section of the column. The inert gas present which carries the acrylic acid vapor from the pyrolyzer exits the top of fractional condensation column. The column is typically operated at pressures of 0.8-3 bars and temperatures in the range of −40° C. to 450° C. In a further embodiment, the higher boiling condensables or heavies (diacrylic acid, heat transfer fluid) from the lower section of the column are recycled back to the pyrolysis chamber and either converted to acrylic acid vapor (in the case of the diacrylic acid) or combined with fresh P3HP biomass (in the case of heat transfer fluid). After fractional condensation or absorption/distillation, the acrylic acid liquid can be further purified by distillation producing a crude mixture that is 99% acrylic and/or crystallization which produces a mixture that is >99% acrylic acid The acrylic acid vapor may alternately be separated by first absorbing (in a counter-current absorption column) into a higher boiling solvent ($T_b$>160° C.) in which acrylic acid liquid has a high solubility. Such solvents include water, biphenyl, diphenyl ether, dimethyl phthalate, ethylhexanoic acid, N-methylpyrrolidone or mixtures of these. The mixture is then sent through a distillation column to separate out the absorption solvent forming the crude acrylic acid and then sent to crystallization to produce a high purity acrylic acid.

In certain embodiments, a polymerization inhibitor is added to the condensed acrylic acid vapor prior, during and after separation in order to prevent the acrylic acid from reacting with itself which fouls the processing equipment. Typical polymerization inhibitors include 0.001-1% by weight in water of hydroquinone, hydroquinone monomethyl ether, tert-butylphenols or nitrosophenols, 1-oxyl-2,2,6,6-tetramethylpiperindin-4-ol, methylene blue, phenothiazine, salicylate, copper salts or mixtures of these.

In certain embodiments, recovery of the catalyst from the thermolyzed P3HP biomass is further included in the processes of the invention. For example, when a $NaHSO_4$ catalyst is used calcination is a useful recovery technique. Calcination is a thermal treatment process that is carried out on minerals, metals or ores to change the materials through decarboxylation, dehydration, devolatilization of organic matter, phase transformation or oxidation. The process is normally carried out in reactors such as hearth furnaces, shaft furnaces, rotary kilns or more recently fluidized beds reactors. Typically calcination temperatures are in the range of 800-1000° C. but calcinations can also refer to heating carried out in the 200-800° C. range.

To recover the catalyst from the biomass after recovery of the acrylic acid when there is a liquid heat transfer fluid present, one would transfer the spent biomass residue directly from pyrolysis or torrefaction into a filter apparatus in order to separate out the heat transfer fluid. The precipitate from the filter apparatus would then be conveyed to a calcining reactor and continue heating the biomass residue in air to 300-650° C. for a period of time to remove all traces of the organic biomass.

In certain embodiments, the process is selective for producing acrylic acid product with a relatively small amount of undesired side products (e.g., dimerized product of acrylic acid (diacrylic acid), other higher molecular weight oligomers of acrylic acid or other side products). For example, in some embodiments the use of a specific catalyst in a sufficient amount will reduce the production of undesired side products and increase the yield of acrylic acid by at least 1.3 fold. In some embodiments, the production of undesired side products will be reduced to at least 30%, at least 20%, at least 10%, at least 5% at least 1%, or at least 0.1%. In certain embodiments, the undesired side products will be less than 5% of the recovered acrylic acid, less than 4% of the recovered acrylic acid, less than 3% of the recovered acrylic acid, less than 1% of the recovered acrylic acid, or less than 0.1% of the recovered acrylic acid.

The processes described herein can provide a yield of acrylic acid expressed as a percent yield, for example, when grown from glucose as a carbon source, the yield is up to 95% based on grams of acrylic acid recovered per gram of P3HP contained in the biomass fed to the process (reported as percent). In other embodiments, the yield is in a range between 40% and 95%, for example between 50% and 70%, or between 60% and 70%. In other embodiment, the yield is about 75%, about 70%, about 65%, about 60%, about 55%, about 50%, about 45% or about 40%.

As used herein, "acrylic acid" refers to the compound with the following chemical structure:

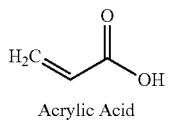

Acrylic Acid

The term "acrylic acid product" refers to a product that contains at least 70 up to 100 weight percent acrylic acid. For example, in a certain embodiment, the acrylic acid product may contain 95% by weight acrylic acid and 5% by weight side products. In some embodiments, the amount of acrylic acid in the acrylic acid product is at least 71% by weight, at least 72% by weight, at least 73% by weight, at least 74% by weight, at least 75% by weight, at least 76% by weight, at least 77% by weight, at least 78% by weight, at least 79% by weight, at least 80% by weight, 81% by weight, at least 82% by weight, at least 83% by weight, at least 84% by weight, at least 85% by weight, at least 86% by weight, at least 87% by weight, at least 88% by weight, at least 89% by weight, at least 90% by weight, 91% by weight, at least 92% by weight, at least 93% by weight, at least 94% by weight, at least 95% by weight, at least 96% by weight, at least 97% by weight, at least 98% by weight, at least 99% by weight or at least 100% by weight. In particular embodiments, the weight percent of acrylic acid product produced by the processes described herein is 85% or greater than 95%.

In other embodiments, the acrylic acid product can be further purified if needed by additional methods known in the art, for example, by condensation, fractional condensation, distillation, reactive distillation (e.g., the acrylic acid product is acidified first to oxidize certain components (e.g., for ease of separation) and then distilled) by filtering, treatment with activated carbon for removal of color and/or odor bodies, by ion exchange treatment, by liquid-liquid extraction—with an acrylic acid immiscible solvent (e.g., nonpolar solvents, like cyclopentane or hexane) to remove fatty acids etc., for purification after acrylic acid recovery, by crystallization, by vacuum distillation, by extraction distillation or using similar methods that would result in further purifying the acrylic acid product to increase the yield of acrylic acid. Combinations of these treatments can also be utilized for increasing the yield of the acrylic acid or acrylic acid product.

As used herein, the term "residual biomass" refers to the biomass plus any heat transfer fluid after PHA conversion to the small molecule intermediates. The heat transfer fluid is then separated from the biomass by filtering, centrifugation, solvent extraction or other separation means known in the arts. The biomass may then be converted via torrefaction to a useable, fuel, thereby reducing the waste from PHA production and gaining additional valuable commodity chemicals from typical torrefaction processes. The torrefaction is conducted at a temperature that is sufficient to densify the residual biomass. In certain embodiments, processes described herein are integrated with a torrefaction process where the residual biomass continues to be thermally treated once the volatile chemical intermediates have been released to provide a fuel material. Fuel materials produced by this process are used for direct combustion or further treated to produce pyrolysis liquids or syngas. Overall, the process has the added advantage that the residual biomass is converted to a higher value fuel which can then be used for the production of electricity and steam to provide energy for the process thereby eliminating the need for waste treatment.

A "carbon footprint" is a measure of the impact the processes have on the environment, and in particular climate change. It relates to the amount of greenhouse gases produced.

In certain embodiments, it may be desirable to label the constituents of the biomass. For example, it may be useful to deliberately label with an isotope of carbon (e.g., $^{13}C$) to facilitate structure determination or for other means. This is achieved by growing microorganisms genetically engineered to express the constituents, e.g., polymers, but instead of the usual media, the bacteria are grown on a growth medium with $^{13}C$-containing carbon source, such as glucose, pyruvic acid, etc. In this way polymers can be produced that are labeled with $^{13}C$ uniformly, partially, or at specific sites. Additionally, labeling with $^{14}C$ (by producing polymers from plant derived sugar sources) allows the determination of the exact percentage in plastics that were derived from renewable or modern via ASTM D6866—an industrial application of radiocarbon dating. ASTM D6866 measures the $^{14}C$ content of materials and uses this value to calculate a % biobased content. Since fossil-based materials no longer contain any $^{14}C$ due to radioactive decay processes, ASTM D6866 accurately measures % biobased content and dispel any false claims of biobased content among commercially available products on the market.

Synthesis of P3HP from 3HP

In certain embodiments of the invention, poly-3-hydroxypropionate (P3HP) is chemically synthesized from 3-hydroxypropionate (3HP) monomer then the P3HP is heated to produce an acrylic acid product. The source of 3HP monomer can either be of biological origin e.g. produced from renewable carbon or from petroleum origin or a mixture of 3HP produced from both renewable carbon and petroleum sources. U.S. Pat. Nos. 7,186,541, 8,030,045 and 8,048,624 describe the use of recombinant bacteria which have been transformed to encode and express enzymes that produce 3-hydroxyproprionate either in vivo or in vitro. The transformed cells are then cultured under aerobic or anaerobic conditions using glucose, sucrose, fructose, dextrose, triglycerides, fatty acids or other carbon substrates to produce biobased 3HP. U.S. Pat. No. 8,114,643 describes a method for producing petroleum-based 3HP from microorganisms and plants genetically engineered convert diols by expression of one or more enzymes selected from the groups comprising vicinal dehydratase, aldehyde dehydrogenase, 1,3-propanediol oxidoreductase, glycerol-3-phosphate dehydrogenase and glycerol-3-phosphatase. Since the substrates used to produce the 3HP are petroleum-based themselves (1,2-propanediol, 1,3-propanediol and glycerol), the 3HP will have a biobased content equal to 0%. U.S. Pat. No. 7,714,097 describes a process for converting 3HP to poly-3-hyroxypropionate by first carrying out self condensation of the 3HP (20% wt. in water) in toluene using a p-toluene sulphonic acid catalyst to produce macrocyclic oligomers (trimers of 3HP). The oligomers are then synthesized in dichloromethane using a zinc-alkoxide catalyst to poly-3-hydroxypropionate product. The molecular weight of the P3HP can be from 300 to $3\times10^6$ daltons.

To generate acrylic acid, the P3HP product generated from the chemical synthesis of 3HP as described above is mixed with catalyst and/or heat transfer fluid, then heated under an inert atmosphere to produce acrylic acid vapor which is then recovered by condensation or other methods known in the art. The biobased content of the resulting acrylic acid as determined by ASTM D6866 is therefore in the range of 0% to 100% depending on the sources of 3HP used to product the P3HP polymer.

Synthesis of Biobased Acrylic Acid Esters and Acrylate Polymers

In certain embodiments, acrylic acid is further reacted to produce acrylic acid esters, acrylic acid polymers, acrylic acid copolymers, acrylic acid ester polymers or acrylic acid ester copolymers. Alkyl acrylates are clear, volatile liquids that are slightly soluble in water and completely soluble in alcohols, ethers and almost all organic solvents. The most common alkyl esters of acrylic acid are methyl-, ethyl, butyl- and 2-ethylhexyl-acrylate. Acrylic acid esters are used chiefly as a monomer or co-monomer in the production of elastomeric fibers, paints, inks, adhesives and coatings for paper and textiles.

There are several synthesis routes to preparing acrylic acid esters from acrylic acid and they include direct esterification, transesterification and enzyme-directed esterification. Numerous processes for direct esterification of acrylic or methacrylic acid can be found in the art (Kirk Othmer *Encyclopedia of Chemical Technology*, $4^{th}$ Ed., 1994 p 301-302; Ullmann's *Encyclopedia of Industrial Chemistry*, 5th Ed., vol. A1, p 167-169). Generally, the direct esterification process uses a homogeneous or heterogeneous acid catalyst to react an alcohol with the hydroxyl group on acrylic acid at elevated temperature. US Patent Application 2004/0147772 describes a process whereby acrylic acid is combined with 5-15% by weight acid (sulfuric, p-toluenesulphonic or methanesulfonic), a thermally treated alcohol (such as methanol, ethanol or butanol), and 0.2-0.5 mmol of a polymerization inhibitor (such as PZT or MEHQ). The addition of the inhibitors and the thermal treatment are to ensure that polymerization of the acrylic acid does not occur. The thermal treatment of the alcohol is carried out at 70-80° C. for 1-2 hrs in order to destroy any peroxides that have formed in the alcohol on standing. Also prior to thermal treatment, the alcohol is dried over molecular sieves to reduce the water concentration to below 1% by weight. The esterification reaction takes place in a heated reactor at 90-100° C. which is connected to a distillation column in order to remove water formed during the esterification helping to drive the reaction to completion. Acidic catalysts can also include solid phase, hetergeneous materials with acidic surfaces such as zeolites, clays, silicas, titanium dioxide, aluminas or even cation exchange resins (DOWEX™ cation exchange resin, AMBERLYST™ cation exchange resin, and NAFION™ cation exchange resin). U.S. Pat. No. 5,426,199 describes the use of sulfonated or phosphonated styrene-divinyl benzene polymer cationic exchange beads as acidic solid phase catalysts for esterification of acrylic acid. Because an excess of alcohol is usually used for the esterification process, this often leads to the formation of ethers when combined with a strong acid catalyst. Use of cation exchange resins minimize the formation of ethers and can be used repeatedly over a long period of time before being expended.

Transesterification involves the reaction of an acrylate ester with an alcohol whereby the ester group present on the acrylate prior to reaction ($R^1$) is substituted with the organic group from the alcohol ($R^2$). The reaction is used to make many different types of polyesters as well biodiesel from fatty acid glycerides. Transesterification can be catalyzed either by strong acids or strong bases. Strong acids catalyze the reaction by donating a proton to the carbonyl group, thus making it a more potent electrophile, whereas bases catalyse the reaction by removing a proton from the alcohol, thus making it more nucleophilic. Esters with larger alkoxy groups can be made from methyl or ethyl acrylic acid esters in high purity by heating the mixture of ester, acid/base, and large alcohol and evaporating the small alcohol to drive equilibrium.

One disadvantage to using catalysts that are strong acids (e.g., $H_2SO_4$) with acrylic acid esters is that there is the potential of causing the acrylic acid ester to polymerize before transesterification takes place especially when the reaction temperature is above 100° C. U.S. Pat. No. 5,827,939 describes the use of heteropolyacid catalysts for direct liquid phase transesterification of acrylic acid esters or direct esterification of acrylic acid which overcomes these limitations by preventing the formation of unwanted side products with high conversion and selectivity. The heteropolyacid catalysts sited in the patent include $H_3PMo_{12}O_{40}$, $H_3PW_{12}O_{40}$ and $H_4SiW_{12}O_{40}$. These can be reused after each reaction and are more environmentally friendly and less caustic than mineral acid catalysts. The transesterification reaction is carried out in a solvent such as MIBK, benzene, hexane or heptane which forms an azeotrope with the alcohol that is generated during the reaction. The water and solvent are then distilled off to remove them from the final acrylate ester. Even though polymerization of the acrylate is minimized, an inhibitor is also usually added such as PZT or MEHQ.

U.S. Pat. No. 5,763,644 describes the use of basic catalysts for the transesterification of methyl methacrylate with polyols such as ethylene glycol or ethoxylated bisphenol A. The transesterification catalysts included mostly potassium hydroxide and alkoxide compounds such as potassium hydroxide, potassium methoxide or potassium ethoxide. The reaction takes place at temperatures as low as 75-80° C. However even under these conditions, a polymerization inhibitor such as PZT or hydroquinone are added. The patent specifies that inhibitors with acidic hydrogen's are to be avoided as they slow down the transesterification reaction rate.

Esterification and transesterification of acrylic monomers and polymers can also take place via enzyme-mediated reaction. Several patents and publications outline the conditions and enzymes useful for carrying out the reactions (Canadian Patent No. 2,631,264; European Patent No. A099229; Pavel et. al (2003), *Makromol. Chem.*, 194, p 3369-3376; Inprakon et. al. (2001), *Designed Monomer and Polymer*, vol. 4, p 95-106). Enzymes that have been used for transesterification or esterification reactions are generally lipases from *Candida cylindracea, Candida antarctica, Rhizomocor miehei*, and *Thermomyces lanuginsoa*. Lipases that are immobilized such as found in the catalyst Novozym® 435 (Novozymes Inc.) which use the lipase from *Candida antarctica* are also useful as catalysts for the transesterification or esterification of acrylates (Warwel et. al. (1996), *Biotechnology Techniques*, vol. 10, no. 4, p 283-286). Typical reaction conditions for use of the catalyst require that the acrylate monomer or polymer be dissolved in a suitable solvent such as toluene, along with the alcohol or polyol to be reacted. Alternatively, the acrylate can be dissolved in the alcohol (added in excess) taking place in the esterification reaction as the solvent. The mixture is then heated with stirring under mild conditions (about 60° C.-85° C.) for up to 24 hours. The mixture is then filtered to remove the catalyst and the mixture distilled or precipitated with a nonsolvent to separate out the acrylate ester. Yields are reported to be in the 65-94% range.

In certain embodiments, acrylic acid esters can also be directly produced from dry biomass containing polymers such as poly-3-hydroxypropionate (P3HP) by mixing the biomass+polymer with an excess of a $C_1$-$C_{12}$ alcohol (petroleum based or biobased) and an esterification catalyst (sulfuric acid, hydrochloric acid, phosphoric acid, trifluoroacetic acid, p-toluene sulfonic, methane sulfonic, dibutyl tin laurate, zinc oxide, zinc chloride, iron chloride, zeolites, aluminas, silicas, titanium dioxide, clays or ion exchange resins such as DOWEX™, AMBERLYST™ resin acid catalyst and NAFION™ resin), heating the mixture to reflux for up to 24 hours with removal of water, and then separating the acrylic acid ester by distillation or other separation methods known in the art. This type of reaction is termed a "one-pot synthesis" or "telescoping synthesis" whereby a single reactant (P3HP in this case) is subjected to successive sequential chemical reactions in a single reaction vessel. This is much desired as it avoids lengthy separation and purification processes of chemical intermediates which improves reaction efficiency by saving both time and cost. The catalyst in this reaction facilitates both the transesterification reaction of the alcohol with the P3HP polymer forming the ester intermediate of 3-hydroxypropionate and dehydration of the intermediate to form the acrylic acid ester. The reaction scheme for the process which can be carried out either on a batch or continuous basis is shown below for the telescoping synthesis reaction of biomass+P3HP with n-butanol using $H_2SO_4$ as the catalyst:

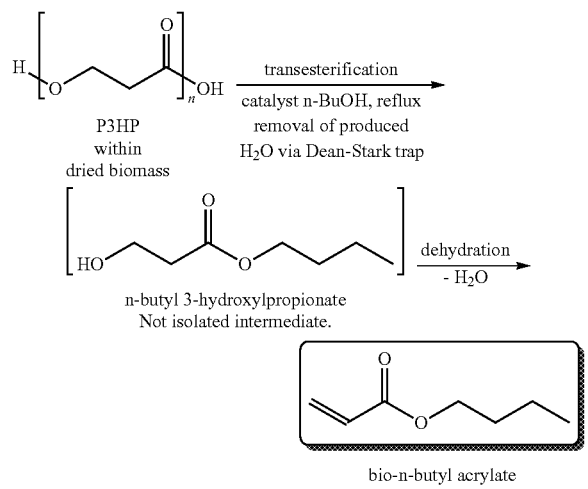

The procedures for preparing polymers and copolymers from acrylate monomers is well known in the prior art. The steps generally include dissolving the acrylate monomer in a solvent, adding a free radical initiator, heating the mixture over a period of time then recovering the acrylate polymer by precipitation and washing. U.S. Pat. Nos. 4,085,264 and 4,301,266 describe procedures for production of low molecular weight ($M_w$<4000) acrylic acid and methacrylic acid polymers. The polymerization is generally carried out in organic solvents such as toluene, dimethyl formamide, methylene dichloride, isopropanol or water. Typical free radical initiators include azo-bis-isobutylnitrile (AIBN), t-butyl peroxide, benzoyl peroxide and 4,4'-dinitrobenzoyl peroxide. Equal parts polymer and solvent are mixed together along with ~0.1-0.5% initiator. The mixture is then heated to 120-200° C. under reduced pressure. The polymer is recovered by removing the solvent either by thin film evaporation or spray drying. The final step is to neutralize the polymer with a base such as KOH.

U.S. Pat. Nos. 3,872,063 and 4,656,222 describe the production of very high molecular weight acrylates ($M_w$>1×$10^6$) using aqueous emulsion polymerization. Copolymerization of acrylic acid with acrylamide can also be made using this synthesis technique. A free radical initiator is required in this reaction as well as a surfactant to help stabilize the emulsion during and after polymerization. U.S. Pat. No. 3,872,063 uses sorbitol monostearate both as the initiator catalyst and the emulsion stabilizer.

To synthesize water absorbing resins based predominantly on acrylic acid monomer, the free radical reaction takes place as a homogeneous aqueous solution, as a gel polymerization or as a suspension of the monomer in water (U.S. Pat. No. 7,157,598). Typically a portion of the acrylic acid monomer is present in the alkali metal salt form. The initiators utilized are water soluble organo peroxides, organohydrogen peroxides, persulfate compounds, perborate compounds and azo compounds. Mixtures of these free radical initiators can also be utilized in the synthesis. To prepare a superabsorbent polymer di, tri or polyfunctional monomers are also added during the synthesis of the acrylic acid polymer such as N,N'-methylene bisacrylamide, trimethylolpropane triacrylate, ethylene glycol di(methyacrylate) or triallylamine.

The di- or poly-functional monomer compounds function as crosslinks for the polyacrylic acid polymer chains, thereby rendering them water insoluble, yet able to swell in the presence of water forming what is known in the art as a hydrogel.

An important characteristic of the synthetic superabsorbent polymers of the invention is the permeability or flow conductivity of a zone or layer of the polymer particles when swollen with body fluids. This permeability or flow conductivity is defined herein in terms of the Saline Flow Conductivity (SFC) value of the superabsorbent polymer. SFC measures the ability of the swollen hydrogel zone or layer to transport or distributes body fluids under usage pressures. It is believed that when a superabsorbent polymer is present at high concentrations in an absorbent member and then swells to form a hydrogel under usage pressures, the boundaries of the hydrogel come into contact, and interstitial voids in this high-concentration region become generally bounded by hydrogel. When this occurs, it is believed the permeability or flow conductivity properties of this region are generally reflective of the permeability or flow conductivity properties of a hydrogel zone or layer formed from the superabsorbent polymer alone. It is further believed that increasing the permeability of these swollen high-concentration regions to levels that approach or even exceed conventional acquisition/distribution materials, such as wood-pulp fluff, can provide superior fluid handling properties e.g. decreasing the incidents of leakage such as from a diaper. Higher SFC values also are reflective of the ability of the formed hydrogel to acquire body fluids under normal usage conditions.

The SFC value of the synthetic superabsorbent polymers derived from renewable resources useful in the invention is at least about $30 \times 10^{-7}$ $cm^3$ sec/g. In other embodiments, the SFC value of the superabsorbent polymers is at least about $50 \times 10^{-7}$ $cm^3$ sec/g. In other embodiments, the SFC value of the superabsorbent polymers is at least about $100 \times 10^{-7}$ $cm^3$ sec/g. Typically, these SFC values are in the range of from about $30 \times 10^{-7}$ to about $1000 \times 10^{-7}$ $cm^3$ sec/g. However, SFC values may range from about $50 \times 10^{-7}$ to about $500 \times 10^{-7}$ $cm^3$ sec/g or from about $50 \times 10^{-7}$ to about $350 \times 10^{-7}$ $cm^3$ sec/g. US Patent Application No. 2011/0319849 describes the test procedures for determining the SFC value of superabsorbent materials and products.

Another important characteristic of the superabsorbent polymers of the invention is their ability to swell against a load. This capacity versus a load is defined in terms of the superabsorbent polymer's Absorption Against Pressure (AAP) capacity. When a superabsorbent polymer is incorporated into an absorbent member at high concentrations, the polymer needs to be capable of absorbing large quantities of body fluids in a reasonable time period under usage pressures. Usage pressures exerted on the superabsorbent polymers used within absorbent article include both mechanical pressures (e.g., exerted by the weight and motions of a wearer, taping forces, etc.) and capillary pressures (e.g., resulting from the acquisition component(s) in the absorbent core that temporarily hold fluid before it is absorbed by the superabsorbent polymer).

The AAP capacity of absorbent polymer is generally at least about 15 g/g. In certain embodiments, the AAP capacity of absorbent polymer is generally at least about 20 g/g. Typically, AAP values range from about 15 to about 25 g/g. However, AAP values may range from about 17 to about 23. US Patent Application No. 2011/0319849 describes the test procedures for determining the AAP capacity of superabsorbent materials and products.

Polymers Derived from Renewable Resources

It may be desirable to label the constituents of the biomass or starting chemicals. For example, it may be useful to deliberately label with an isotope of carbon (e.g., $^{13}C$) to facilitate structure determination or for other means such as origin and certainly of renewable content. In one way, this is achieved by growing microorganisms genetically engineered to express the constituents, e.g., polymers, but instead of the usual media, the bacteria are grown on a growth medium with $^{13}C$-containing carbon source, such as glucose, pyruvic acid, or other feedstocks discussed herein. In this way polymers can be produced that are labeled with $^{13}C$ uniformly, partially, or at specific sites.

Additionally, labeling allows the exact percentage in bioplastics that came from renewable sources (e.g., plant derivatives) determined via ASTM D6866—an industrial application of radiocarbon dating. ASTM D6866 measures the Carbon 14 content of biobased materials; and since fossil-based materials no longer have Carbon 14, ASTM D6866 can effectively dispel inaccurate claims of biobased content. In this analysis technique for determination of Renewable resources, the ratio of $^{14}C$ to total carbon within a sample ($^{14}C/C$) is measured. Research has noted that fossil fuels and petrochemicals generally have a $^{14}C/C$ ratio of less than about $1\times10^{-15}$. However, polymers derived entirely from renewable resources typically have a $^{14}C/C$ ratio of about $1.2\times10^{-12}$. Other Suitable techniques for $^{14}C$ analysis are known in the art and include accelerator mass spectrometry, liquid scintillation counting, and isotope mass spectrometry. These techniques are described in U.S. Pat. Nos. 3,885,155; 4,427,884; 4,973,841; 5,438,194; and 5,661,299. Accuracy of radioanalytical procedures used to determine the biobased content of manufactured products is outlined in Norton et al, Bioresource Technology, 98 1052-1056 (2007), incorporated by reference.

The application of ASTM D6866 to derive a "bio-based content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of biomass material present in the sample.

The modern reference standard used in radiocarbon dating is a NIST (National Institute of Standards and Technology) standard with a known radiocarbon content equivalent approximately to the year AD 1950. The year AD 1950 was chosen because it represented a time prior to thermo-nuclear weapons testing, which introduced large amounts of excess radiocarbon into the atmosphere with each explosion (termed "bomb carbon"). The AD 1950 reference represents 100 pMC.

In the compositions of the invention for making articles the bio-based chemicals comprise at least about 50% (e.g., at least about 60%, at least about 65%, at least about 70%, at least about 75%, at least about 80%, at least about 85%, at least about 90%, or at least about 95%, at least about 96%, at least about 97%, at least about 98%, at least about 99%, up to 100%) bio-based content based on the total weight of the composition. In this regard, the synthetic polymer is composed of a sufficient amount of bio-based components (i.e., the precursors are substantially composed of materials derived from renewable resources), and the composition comprises a sufficient amount to achieve the desired bio-based content level.

Biobased Acrylic Acid Products

Products, including commercial and consumer products, obtained from the polymers are also encompassed. For example, acrylic acid and its esters readily combine with themselves or other monomers (e.g. acrylamides, acrylonitrile, vinyl, styrene, and butadiene) by reacting at their double bond, forming homopolymers or copolymers which are used in the manufacture of various plastics, paper manufacture and coating, exterior house paints for wood and masonry coatings for compressed board and related building materials, flocculation of mineral ore fines and waste water, and treatment of sewage, printing inks, interior wall paints, floor polishes, floor and wall coverings, industrial primers, textile sizing, treatment and finishing, leather impregnation and finishing and masonry sealers, coatings, adhesives, elastomers, as well as floor polishes, and paints. Acrylic acid is also used in the production of polymeric materials such polyacrylic acid, which is a major component of superabsorbent diapers.

EXAMPLES

The present technology is further illustrated by the following examples, which should not be construed as limiting in any way.

Experimental Methods

Measurement of Thermal Degradation Behavior by Thermogravimetric Analysis (TGA)

The thermal weight loss versus time for biomass+polymer was measured using a TA Instruments Q500 Thermogravimetric Analyzer (TGA). TGA is a technique commonly used to measure the thermal degradation behavior of materials such as PHA's. The instrument consists of a sensitive balance from which a sample is suspended. A furnace is then brought up around the sample and programmed to heat at a specified rate (ramp conditions) or to a certain temperature and hold (isothermal conditions). A purge gas is swept across the sample during heating which is typically nitrogen or air. As the sample is heated, it begins to lose weight which is recorded by the balance. At the end of the analysis, the results can then be plotted as percent sample weight loss versus temperature or time. When plotted as weight loss versus time, the rate of degradation can then be determined from the slope of this curve. For the following examples, 10-30 mg of dry biomass+polymer was weighed into a platinum pan and then loaded onto the TGA balance. The purge gas used was nitrogen at a flow rate of 60 ml/min During the analysis, the biomass sample was preheated from room temperature to 300° C. at a heating rate of 10° C./min. The data was then plotted as % sample weight loss vs. time and the thermal degradation rate calculated from the initial slope of the weight loss curve.

Measurement of Thermal Degradation Products by Pyrolysis-Gas Chromatography-Mass Spectroscopy (Py-GC-MS).

In order to identify and semi-quantitate the monomer compounds generated from either dry biomass+polymer or polymer while being heated at various temperatures, an Agilent 7890A/5975 GC-MS equipped with a Frontier Lab PY-2020iD pyrolyzer was used. For this technique, a sample was weighed into a steel cup and loaded into the pyrolyzer autosampler. When the pyrolyzer and GC-MS were started for a run, the steel cup was automatically dropped into the pyrolyzer which had been set to a specific temperature. The sample was then held in the pyrolyzer for a short period of time while volatiles were released by the sample. The volatiles were then swept using helium gas into the GC column where they condensed onto the column which was maintained at a temperature of 120° C. Once the pyrolysis was completed, the GC column was heated at a certain rate in order to elute the volatiles released from the sample. The volatile compounds were then swept using helium gas into an electro ionization/mass spectral detector (mass range 10-700 daltons) for identification and quantitation.

For the following examples, 200-500 µg of dry biomass was weighed into a steel pyrolyzer cup using a microbalance. The cup was then loaded into the pyrolyzer autosampler. The pyrolyzer was programmed to heat at a programmed temperature ranging from 250-350° C. for a duration of 0.2 minutes. The GC column used in the examples was a Hewlett-Packard HP-INNOwax column (length 30 m, ID 0.25 µm, film thickness 0.25 µm). The GC oven was then programmed to hold at 120° C. for 5 minutes, heat from 120° C. to 240° C. at 10° C./min, then hold for 6 min Total GC run time was 23 minutes. A split ratio of 50:1 was used during injection of the pyrolyzate vapor onto the GC column. Peaks appearing in the chromatogram plot were identified by the best probability match to spectra from a NIST mass spectral library. Acrylic acid 'purity' was estimated by taking the ratio of the area counts or percent peak area for the acrylic acid peak and dividing it by the area counts or percent peak area for acrylic acid dimer peak.

These examples describe a number of biotechnology tools and methods for the construction of strains that generate a product of interest. Suitable host strains, the potential source and a list of recombinant genes used in these examples, suitable extrachromosomal vectors, suitable strategies and regulatory elements to control recombinant gene expression, and a selection of construction techniques to overexpress genes in or inactivate genes from host organisms are described. These biotechnology tools and methods are well known to those skilled in the art.

Example 1. Generation of Acrylic Acid from the Pyrolysis of a Genetically Engineered Biomass Producing Poly-3-Hydroxypropionate (P3HP)

Biomass containing poly-3-hydroxypropionate was produced in a 1 L DASGIP (Jülich, Germany) bioreactor system comprised of a BioBlock equipped with 1 liter vessels and DASGIP Control 4 software and using a genetically modified *E. coli* strain specifically design for production of P3HP. Cells were cultivated under aerobic conditions utilizing glucose minimal medium and glucose syrup as a carbon feed source for fed-batch operation. Examples of complete exemplary fermentation conditions, media, and feed conditions are described in U.S. Pat. Nos. 6,316,262; 6,689,589; 7,081,357; and 7,229,804 incorporated by reference herein. In addition to the referenced media, vitamin B12 (CAS #68-19-9, Sigma-Aldrich) was also added to the fermentation run at final broth concentrations ranging from 1 to 100 mM as a required cofeed for a glycerol dehydratase enzyme. *E. coli* cultivations resulted in fermentation broths which had a P3HP titer of approximately 30-60 grams of P3HP per liter of broth. On a dry basis, the weight percent P3HP in the biomass was estimated at approximately 60%.

After generation of the P3HP biomass, the broth was washed by first centrifuging the P3HP biomass at 7000 rpm for 20 minutes, decanting the separated liquid, adding back an equal volume of DI water, resuspending the biomass in the added DI water and then recentrifuging. This was repeated three times in order to remove as many of the dissolved salts from the fermentation media prior to pyrolysis as possible. After the final wash, the P3HP biomass was dried at room temperature overnight and then cryogenically ground with liquid nitrogen to a powder using a Spex CertiPrep 6870 Freezer Mill. Table 1 shows results for analysis of the unwashed and washed-dried-ground (WDG) P3HP biomass by Inductively-Coupled Plasma-Mass Spectroscopy (ICP-MS). The measurement was carried out to assess the effectiveness of the washing process for removal of unwanted metal ions from the fermentation media. For this analysis, the unwashed P3HP biomass sample was also dried at room temperature overnight and ground prior to measurement.

TABLE 1

ICP-MS quantitative analysis for total metal ions in unwashed and DI water washed P3HP biomass.

| Metal Ion | Unwashed P3HP biomass | Washed P3HP biomass* |
|---|---|---|
| Calcium | <2 ppm | 47 ppm |
| Magnesium | 392 ppm | 422 ppm |
| Potassium | 18804 ppm | 1488 ppm |
| Sodium | 3277 ppm | 199 ppm |
| Copper | 20 ppm | 12 ppm |
| Iron | 132 pm | 81 ppm |
| Zinc | 34 ppm | 29 ppm |

*Triple washed with DI water

The results in Table 1 show that the DI water washing step reduced the concentration of the potassium and sodium ions remaining in the P3HP biomass after fermentation by a factor of 13-16. The concentration of calcium, magnesium, copper, iron and zinc metals in the P3HP biomass did not appear to change significantly after washing with DI water however.

Figure 2:
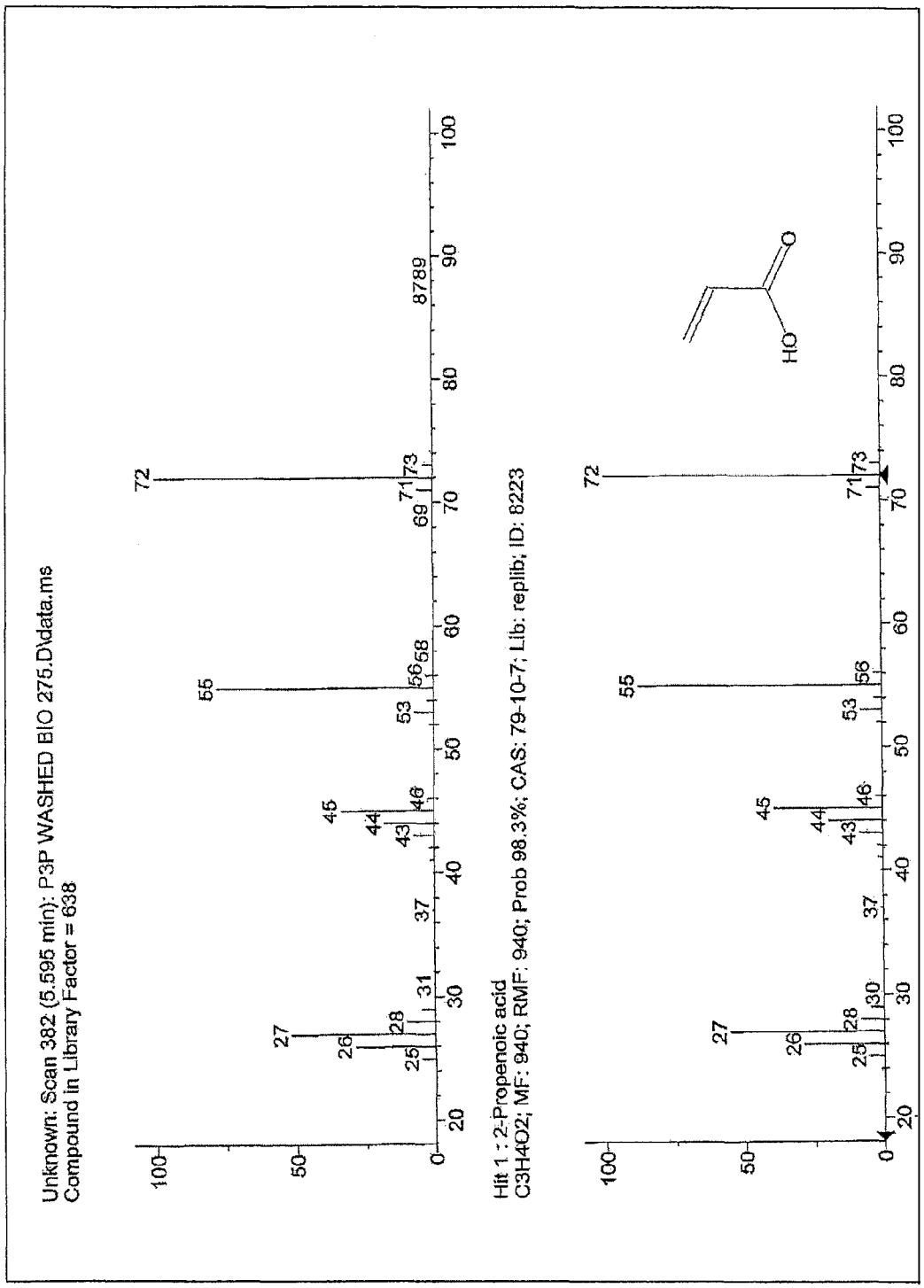
FIG. 2 is a mass spectrum of the GC peak at 5.6 min. retention time from FIG. 1 (upper). Mass spectral library match to 5.6 min peak (lower) showing it was identified as acrylic acid (2-propenoic acid).
Figure 3:
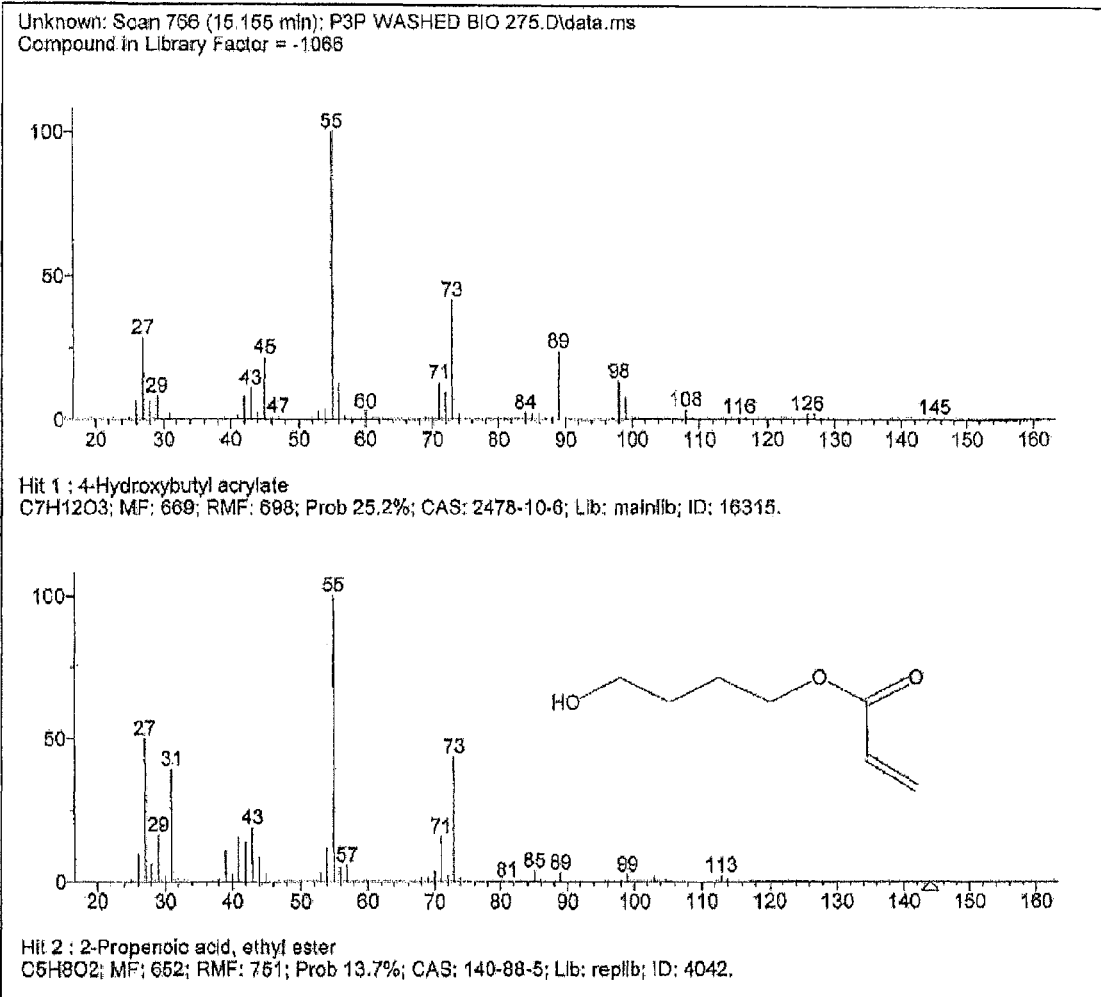
FIG. 3 is a mass spectrum of the GC peak at 15.2 min. retention time from FIG. 1 (upper) and mass spectrum from diacrylic acid (lower) generated by heating acrylic acid in air with 1000 ppm hydroquinone at 120-130° C. for 10 hours.

The WDG P3HP biomass was then analyzed by pyrolysis-GC-MS at a pyrolysis temperature of 275° C. FIG. 1 shows the GC plot of the pyrolyzate products generated from the P3HP biomass at 275° C. The main peaks observed were found at retention times of 5.6 minutes and 15.2 minutes and corresponded to acrylic acid monomer (CAS #79-10-7) and the diacrylic acid or dimer of acrylic acid monomer (CAS#24615-84-7) respectively. FIG. 2 shows the mass spectrum and best spectral library match to the GC peak @5.6 minutes confirming the identification of the peak as acrylic acid monomer. FIG. 3 shows the mass spectrum for the GC peak @15.2 minutes as well as the mass spectrum for pure diacrylic acid that was generated by heating liquid acrylic acid monomer in air with 1000 ppm hydroquinone at 120-130° C. for 10 hours (after the 10 hours, GC-MS analysis of the liquid showed it to be composed of approximately 25% acrylic acid monomer and 75% diacrylic acid). The most prominent mass spectral peaks for the diacrylic acid were found at 45, 55, 73 and 89 m/z which corresponded to the mass fragments $COOH^+$, $CH_2=CHCO^+$, $CH_2CH_2COOH^+$ and $OCH_2CH_2COOH^+$. The molecular weight of the diacrylic acid was calculated to be 144 amu and a mass ion at 145 m/z was detected in the mass spectrum for this compound which could correspond to the protonated diacrylic acid molecule.

Figure 4:
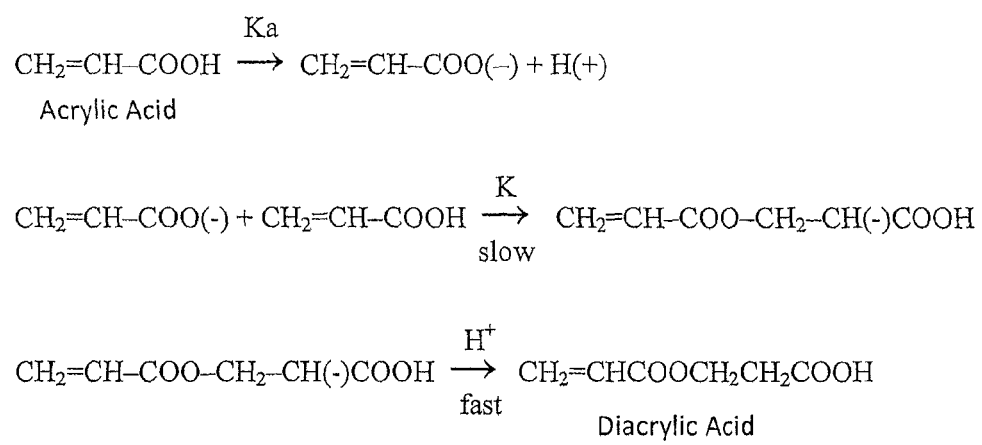
FIG. 4 is a reaction scheme showing the formation of diacrylic acid during production of acrylic acid from oxidation of propene.

FIG. 4 shows the mechanism of diacrylic acid formation during production of acrylic acid from oxidation of propene (BASF technical data sheet found on the web at: 2.basf.us/businesses/chemicals/acrylates/pdfs/acry-dim.pdf. The reaction is a second order Michael addition type where an acrylic acid nucleophile is generated which then reacts with the double bond of another acrylic acid molecule. The reaction occurs spontaneously in the liquid state and cannot be chemically inhibited or reversed. It was also found that both temperature and moisture concentration impact the rate of diacrylic acid formation. Therefore diacrylic acid formation can be minimized but not eliminated by controlling the temperature and moisture. The reaction rates for the formation of higher molecular weight acrylic acid species (trimer, tetramer etc.) are so slow that they are not generated at any appreciable amounts in recovered acrylic acid. The pyrolysis-GC-MS data shown in FIG. 3 indicated that for the pyrolysis at 275° C. of WDG P3HP biomass, a significant amount of diacrylic acid was generated in the vapor phase as acrylic acid was formed. The ratio of acrylic acid monomer to diacrylic acid was calculated to be 2.4 which equated to approximately 29% diacrylic acid formation. In commercial production of acrylic acid from propene, the presence of diacrylic acid has been linked to problems with molecular weight control, processing problems and product performance variation of acrylic polymers. Therefore, elimination of the diacrylic acid as an impurity in acrylic acid is desired.

Other minor impurity compounds were found to be generated during pyrolysis of the WDG P3HP biomass such as acetic acid, fatty acids ($C_{16}$ and $C_{18}$) and 2-propenamide. These compounds all originated from the biomass and glucose feed not the P3HP. Propenamide has been found to form by the reaction of amino acids and sugars when they are heated together.

Example 2. Generation of Acrylic Acid from the Pyrolysis of a Genetically Engineered Biomass Producing Poly-3-Hydroxypropionate (P3HP) with Added Catalyst In this example, P3HP biomass samples were prepared by fermentation of genetically engineered microbes as outlined in Example 1. After triple washing the fermentation broth, drying and cryogrinding to a powder, the samples were then combined with various catalysts. The purpose of incorporating the catalysts was to both inhibit the formation of diacrylic acid during pyrolysis of P3HP biomass and increase the conversion rate of P3HP to acrylic acid so that lower pyrolysis temperatures could be utilized.

Samples containing P3HP biomass with a catalyst were prepared for pyrolysis-GC-MS by taking 2 g of the WDG P3HP biomass, adding 4 g of DI water and a 10% aqueous catalyst solution and then resuspending the solids in the liquid. The mixture was then dried in air overnight at room temperature and lyophilized to remove water. The final concentration of catalyst in the dried P3HP biomass samples was 2-5% by weight dry biomass while the final water content was <3% by weight dry biomass. The catalysts evaluated included phosphoric acid ($H_3PO_4$), sulfuric acid ($H_2SO_4$), sodium hydrogen sulfate ($NaHSO_4$), copper sulfate ($CuSO_4$), zinc sulfate ($ZnSO_4$), calcium hydroxide ($Ca(OH)_2$), aluminum chloride ($AlCl_3$), copper chloride ($CuCl_2$) and zinc chloride ($ZnCl_2$). All of the catalysts were purchased from Sigma Aldrich. Prior to pyrolysis, the samples were roughly crushed by hand with a spatula. Pyrolysis of the dried P3HP biomass with catalyst was carried out at both 250° C. and 275° C. Also included as samples were WDG P3HP biomass which contained no catalyst and unwashed-dried P3HP biomass with no catalyst added.

Table 2 summarized the pyrolysis-GC-MS data for the P3HP biomass+catalyst samples analyzed. The data shown includes the peak area percent diacrylic acid formed as well as the acrylic acid/diacrylic acid ratio for each sample. The higher ratio indicated that less diacrylic acid was formed during pyrolysis which was desirable. The results showed several other interesting trends: first, the lower the pyrolysis temperature, the less diacrylic acid that was formed overall during pyrolysis. In most cases, the acrylic acid/diacrylic acid ratio was found to be higher at the 250° C. pyrolysis temperature in comparison to 275° C.; second, the unwashed biomass having high potassium and sodium ions present gave consistently lower diacrylic acid formation at both the 250° C. and 275° C. pyrolysis temperatures; third, two of the mineral acid catalysts, $NaHSO_4$ and $H_2SO_4$ (at 5% loading), were found to unexpectedly suppress the formation of diacrylic acid completely at 250° C. The mineral acids $NaHSO_4$ and $H_2SO_4$ which are strong Bronsted-Lowery acids and even $H_3PO_4$, which is a relatively weaker acid, were in general found to be the best at minimizing the formation of diacrylic acid during pyrolysis of the P3HP biomass. This could be due to the fact that these compounds acted as more efficient proton donors for end capping any acrylic acid anions that formed (see FIG. 4) during pyrolysis thereby stopping the further formation of diacrylic acid. For the sulfuric acid catalyst, it appeared that a combination of low pyrolysis temperature (250° C.) and high concentration (5% by wt) were needed in order to maximize the performance of this catalyst. The outstanding lower temperature performance of $H_2SO_4$ could be due to the fact that sulfuric acid decomposes at 280° C. and therefore becomes inactivated close to or above its decomposition temperature.

TABLE 2

Summary of Pyrolysis-GC-MS results for washed-dried-ground (WDG) P3HP biomass with 5% catalyst by weight (unless specified). Also included are samples for unwashed and washed-dried-ground P3HP biomass with no catalyst included. Pyrolysis temperatures evaluated were 250° C. and 275° C.

| Catalyst | Diacrylic Acid GC Peak Area Percent | | Ratio of Acrylic Acid GC Peak Area/ Diacrylic Acid GC Peak Area | |
|---|---|---|---|---|
| | 250° C. | 275° C. | 250° C. | 275° C. |
| None - WDG P3HP biomass | 33 | 28 | 1.9 | 1.7 |
| None - Unwashed Dried P3HP biomass | 12 | 9 | 6.0 | 6.2 |
| $H_3PO_4$ | 6.4 | 12 | 12 | 5.8 |
| $H_2SO_4$ - 2% in biomass | 16 | 16 | 4.8 | 4.7 |
| $H_2SO_4$ - 5% in biomass | 0 | 17 | — | 4.3 |
| NaHSO4 | 0 | 12 | — | 6.4 |
| $CuSO_4$ | 20 | 27 | 3.8 | 2.5 |
| $ZnSO_4$ | 16 | 19 | 5.2 | 4.0 |
| $Ca(OH)_2$ | 39 | 27 | 1.4 | 1.8 |
| $AlCl_3 \cdot 6H_2O$ | 16 | 22 | 4.6 | 2.9 |
| $CuCl_2$ | 33 | 40 | 1.9 | 1.4 |
| $ZnCl_2$ | 31 | 38 | 1.9 | 1.5 |

The Lewis acid-type sulfate catalysts, $CuSO_4$ and $ZnSO_4$, were found to be moderately effective at minimizing the formation of diacrylic acid during pyrolysis. The Lewis acid-type chloride catalyst, $AlCl_3.6H_2O$, was also found to have some ability to suppress diacrylic acid formation during pyrolysis while the $ZnCl_2$ and $CuCl_2$ catalysts showed poor ability for diacrylic acid suppression. Likewise the calcium hydroxide, which is a strong Bronsted-Lowery base, was shown to promote the formation of diacrylic acid during pyrolysis of P3HP biomass. This compound being a proton acceptor likely facilitated the abstraction of a hydrogen from acrylic acid forming the acrylic acid anion.

Figure 5:
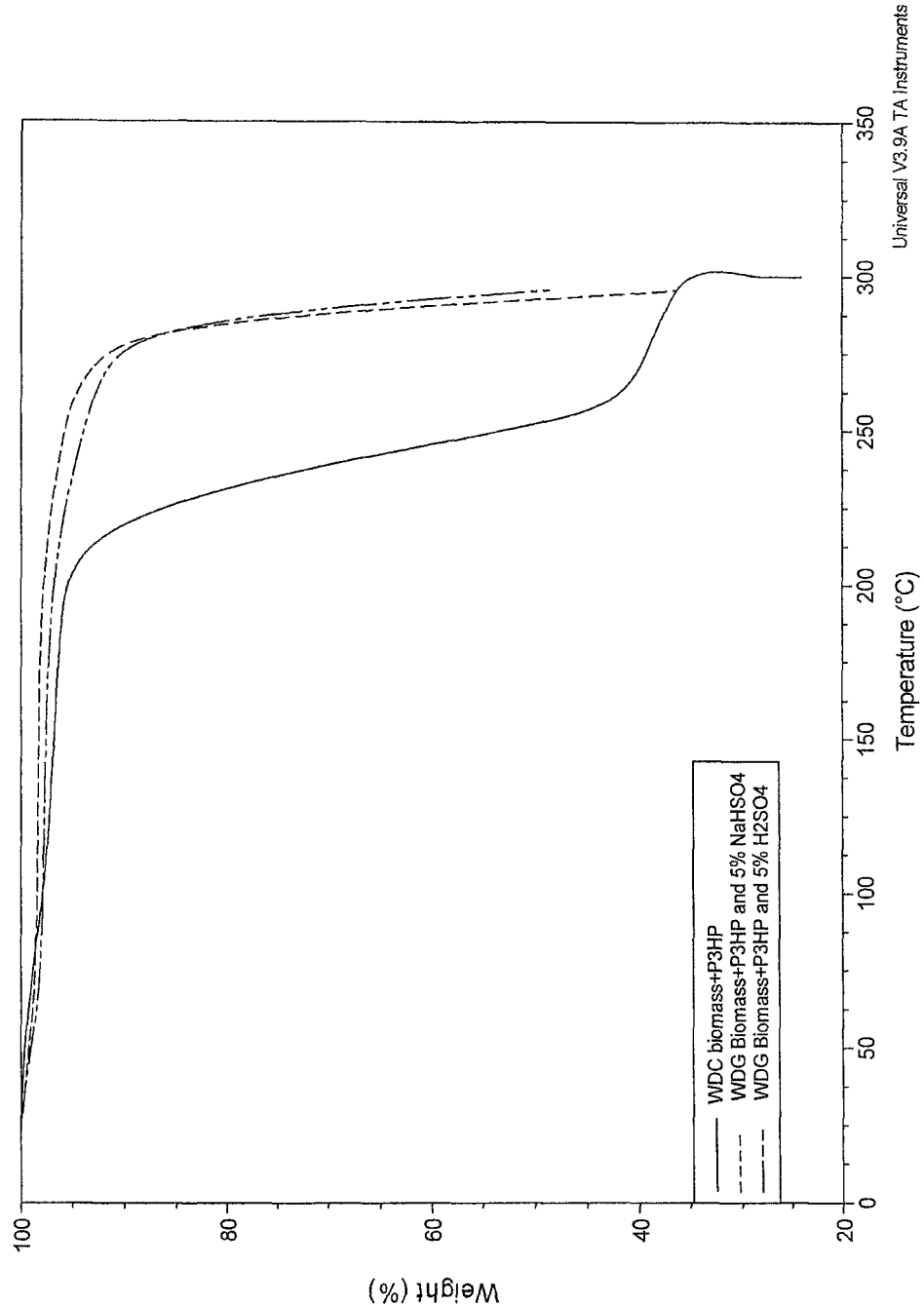
FIG. 5 are thermogravimetric plots of % weight loss versus temperature for washed-dried-ground (WDG) P3HP biomass without catalyst (solid line), with 5% by weight NaHSO$_4$ (dashed line) and 5% by weight H$_2$SO$_4$ (dot-dash line).

Thermal gravimetric Analysis (TGA) was carried out on the WDG P3HP biomass with no catalyst added and with 5% by weight $NaHSO_4$ and $H_2SO_4$ added. The samples were heated from room temperature to 300° C. at 10° C./min under nitrogen and analyzed for the onset temperature for polymer weight loss and the slope of the polymer weight loss versus time (polymer degradation rate). Table 3 summarizes the TGA data collected for these samples and FIG. 5 shows an overlay plot of the TGA curves for the above samples.

TABLE 3

Summary of Thermogravimetric Analysis (TGA) data for WDG P3HP biomass with no catalyst, 5% by wt. $NaHSO_4$ and 5% by wt. $H_2SO_4$ catalyst. Samples were run under nitrogen from room temperature to 300° C. at 10° C./min.

| Sample ID | $T_{onset}$ (° C.) | Polymer Degradation Rate (% Wt loss/min) |
|---|---|---|
| WDG P3HP biomass | 212 | −1.36 |
| WDG P3HP biomass + 5% $NaHSO_4$ | 277 | −4.19 |
| WDG P3HP biomass + 5% $H_2SO_4$ | 280 | −3.11 |

The data in Table 3 shows that addition of $NaHSO_4$ and $H_2SO_4$ to the WDG P3HP biomass increased the rate of thermal degradation of the P3HP polymer and therefore had a catalytic effect on the thermal degradation of P3HP as seen by the more negative slopes of the TGA curves after polymer degradation began (see FIG. 5). However, the temperature at which degradation began e.g. the onset temperature was also shown to shift to higher temperatures by about 60-70° C. with the addition of the $NaHSO_4$ and $H_2SO_4$ catalysts. This could explain the reason why when pyrolysis of a WDG P3HP biomass having 5% wt $H_2SO_4$ at 225° C. was carried out, no acrylic acid was detected by the mass detector within the 23 minute GC-MS analysis time window. WDG P3HP biomass with no $H_2SO_4$ present however when pyrolyzed at 225° C. did show acrylic acid formation with an acrylic acid/diacrylic acid ratio of approximately 5. The best approach therefore to liberate acrylic acid quickly and with low diacrylic acid impurities by pyrolysis may be to use unwashed P3HP biomass with the addition of 5% by wt. $NaHSO_4$ or $H_2SO_4$ at 250° C.

Example 3. Generation of Acrylic Acid from the Pyrolysis of Poly-3-Hydroxypropionate (P3HP) Extracted from Genetically Engineered Biomass In this example, catalyst was mixed directly with P3HP polymer extracted from P3HP biomass material and then analyzed by pyrolysis-GC-MS. P3HP biomass samples were prepared by fermentation from genetically engineered microbes as outlined in Example 1. After triple washing the fermentation broth, drying and cryogrinding to a powder, the samples were mixed with chloroform to give a 5% by weight P3HP biomass solution. The solution was heated to 90° C. for 4-5 hrs, cooled to room temperature, filtered and the solvent evaporated at room temperature. The remaining P3HP polymer solids were further purified by recrystallization as follows: a 10% by weight P3HP solution was prepared with a 90/10 ethanol/water solution then and set to reflux until the polymer was dissolved. The solution was then cooled to precipitate the P3HP and the polymer solid was filtered and dried.

The P3HP with catalyst samples were prepared by first dissolving the purified P3HP polymer in 90/10 chloroform/isopropanol to a final polymer concentration of 0.47% by weight. A 0.25% by weight catalyst solution was then prepared by dissolving the catalyst in DI water. The catalyst solution was then pipetted into the steel pyrolysis sample cups along with the polymer solution at a volume ratio of 10 μl catalyst solution/35 μl P3HP solution. The entire mixture was left to air dried overnight then vacuum oven dried at room temperature to remove any final traces of solvent and water. The catalysts evaluated included phosphoric acid ($H_3PO_4$), sulfuric acid ($H_2SO_4$), copper sulfate ($CuSO_4$), iron sulfate ($FeSO_4$) and calcium hydroxide ($Ca(OH)_2$). All of the catalysts were purchased from Sigma Aldrich. The final concentration of catalyst in the dry samples was approximately 13% by weight P3HP.

The above samples were then analyzed by pyrolysis-GC-MS at pyrolysis temperatures of 275° C., 300° C. and 350° C. After the analysis, the acrylic acid/diacrylic acid ratio was calculated from the GC peak areas at retention times 5.8 minutes for the acrylic acid and 15.3 minutes for the diacrylic acid. Table 4 shows a summary of the pyrolysis-GC-MS data collected for the biologically-produced P3HP polymer with and without catalyst.

TABLE 4

Summary of pyrolysis-GC-MS results for thermolysis of biologically-produced poly-3-hydroxypropionate (P3HP) polymer with the addition of various catalysts. Catalyst concentration was 13% by weight P3HP.

| Catalyst | Ratio of Acrylic Acid Peak Area/Diacrylic Acid Peak Area | | |
|---|---|---|---|
| | 275° C. | 300° C. | 350° C. |
| None | 2.8 | 1.5 | 1.0 |
| $H_3PO_4$ | 38.1 | 9.5 | 4.2 |
| $H_2SO_4$ | 39.9 | 4.6 | 9.1 |
| $FeSO_4$ | 4.7 | 2.1 | 3.0 |
| $CuSO_4$ | 4.7 | 4.5 | 4.8 |
| $Ca(OH)_2$ | 1.1 | 0.9 | 1.9 |

The results shown in Table 4 are very similar to those found for the pyrolysis of the P3HP biomass e.g. as the pyrolysis temperature increased, the acrylic acid/diacrylic acid ratio decreased indicating more diacrylic acid forming from the P3HP polymer during thermolysis; the mineral acids $H_3PO_4$ and $H_2SO_4$ were found to be the best out of all the catalysts tested for suppressing the formation of the diacrylic acid giving very high acrylic acid/diacrylic ratios at 275° C. Addition of $Ca(OH)_2$ as a catalyst increased the formation of diacrylic acid as evidenced by the very low acrylic acid/diacrylic acid ratios. The sample with no addition of catalyst also gave fairly low acrylic acid/diacrylic acid ratios especially at the 350° C. pyrolysis temperature.

Example 4. Larger Scale Batch Production of Acrylic Acid from the Pyrolysis of a Genetically Engineered Microbe Producing Poly-3-Hydroxypropionate In the following example, acrylic acid production from pyrolysis of a fermentation broth+P3HP+catalyst mixture will be outlined showing the ability to produce a high purity, high yield, biobased acrylic acid on the one hundred gram scale.

Biomass containing poly-3-hydroxypropionate (P3HP) was produced in a 20 L New Brunswick Scientific fermenter (BioFlo 4500) using a genetically modified *E. coli* strain specifically designed for high yield production of P3HP from glucose syrup as a carbon feed source. Examples of the *E. coli* strains, fermentation conditions, media and feed conditions are described in U.S. Pat. Nos. 6,316,262; 6,689,589; 7,081,357; and 7,229,804. In addition to the glucose feed, vitamin B12 was also added during the fermentation. The *E. coli* strain generated a fermentation broth which had a PHA titer of approximately 30-60 g of PHA/kg of broth. After fermentation, the broth was washed with DI water by adding an equal volume of water, mixing for 2 minutes, centrifuging and decanting the water. Alternatively the broth can be washed with a 20-30 mM solution of phosphoric acid followed by water washing or by washing with a 0.85 g/l saline solution.

Next, the washed broth was mixed with the catalyst $NaHSO_4$ targeting 5% by wt catalyst per dry weight biomass solids. The mixture was then dried in a rotary kiln at 100-125° C. to a constant weight. Moisture levels in the dried biomass were approximately 1-2% by weight.

Figure 6:
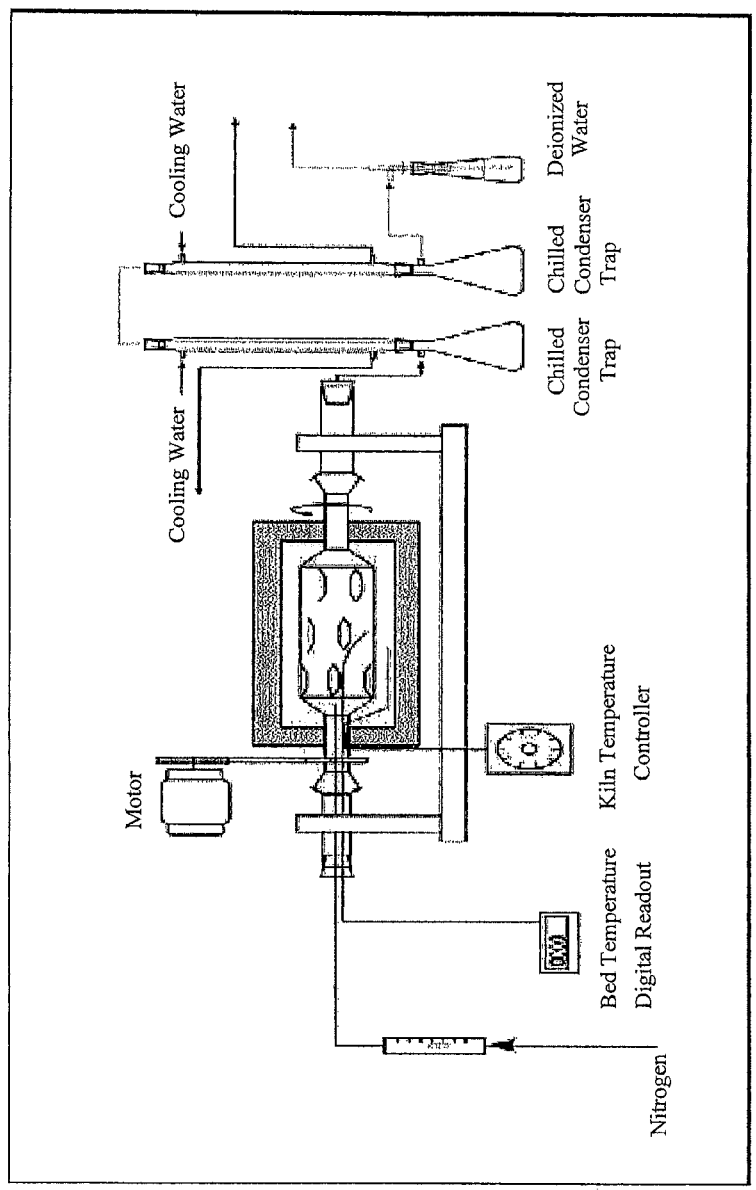
FIG. 6 is a schematic diagram showing lab scale pyrolysis equipment to produce biobased acrylic acid from P3HP biomass.

Pyrolysis of the dried P3HP biomass+$NaHSO_4$ was carried out using a rotating, four inch diameter quartz glass kiln suspended within a clamshell tube furnace. At the start of the process, a weighed sample of dried biomass+P3HP+$NaHSO_4$ was placed inside of the glass kiln and a nitrogen purge flow established. The furnace rotation and heat up were then started. As the temperature of the furnace reached its set point value, vapors generated by the dried biomass+P3HP+$NaHSO_4$ sample were swept out of the kiln by the nitrogen purge and entered a series of glass condensers or chilled traps. The condensers consisted of a vertical, cooled glass condenser tower with a condensate collection bulb located at the its base. A glycol/water mixture held at 0° C. was circulated through all of the glass condensers. The cooled vapors that exited the top of the first condenser were directed downward through a second condenser and through a second condensate collection bulb before being bubbled through a glass impinger filled with deionized water. FIG. 6 shows a schematic diagram of the furnace and gas collection equipment.

For the larger scale pyrolysis experiment, 200 g of dried broth+P3HP+$NaHSO_4$ was first loaded into the quartz kiln at room temperature. The total weight of P3HP biomass was estimated to be 190 g based on $NaHSO_4$ catalyst loading. The wt % P3HP in the mixture was also measured to be approximately 60% (see Doi, *Microbial Polyesters*, John Wiley and Sons, p 23, 1990) based on the dry solids which made the mass of P3HP in the kiln equal to 114 g. The system was then sealed up and a nitrogen purge of approximately 1500 ml/min was established. Power was applied to the furnace and the dried broth+P3HP+$NaHSO_4$ was heated up to the target pyrolysis temperature of 250° C. During pyrolysis, the products of thermal degradation of P3HP biomass, acrylic acid, were collected in the condensate traps below the cooled condensers. Water could be seen to collect initially in each of the collection bulbs. The majority of the liquefied product (>95%) was collected in the first glass collection bulb. Total pyrolysis run time was approximately 60 minutes. The weight of the remaining biomass after pyrolysis was measured to be 10.5 g.

After the completion of the pyrolysis run, the condensates from the condensers were collected and weighed. The results showed that the combined condensate weight was 105 g. Analysis of the condensate by Karl Fisher moisture analysis and GC-MS showed that the condensate contained 3% water, 0.06% fatty acids with the balance of the material being acrylic acid. The acrylic acid product yield ((g of acrylic acid product/g of starting P3HP)×100%) therefore was calculated to be approximately 92%. The GC-MS results also showed that other minor impurities such as acetic acid and amide compounds were also detected as being present in the condensate by GC-MS. The conversion of the P3HP biomass solid to liquid ((g of dry Biomass−g residual Biomass/g of dry Biomass)×100%) was calculated to be 95%. To inhibit any further reaction of the acrylic acid collected during pyrolysis, 0.1% by weight of 4-methoxyphenol (MEHQ, Sigma Aldrich) was added to the pyrolysis condensate.

Example 5. Continuous Production of Biobased Acrylic Acid

Figure 7:
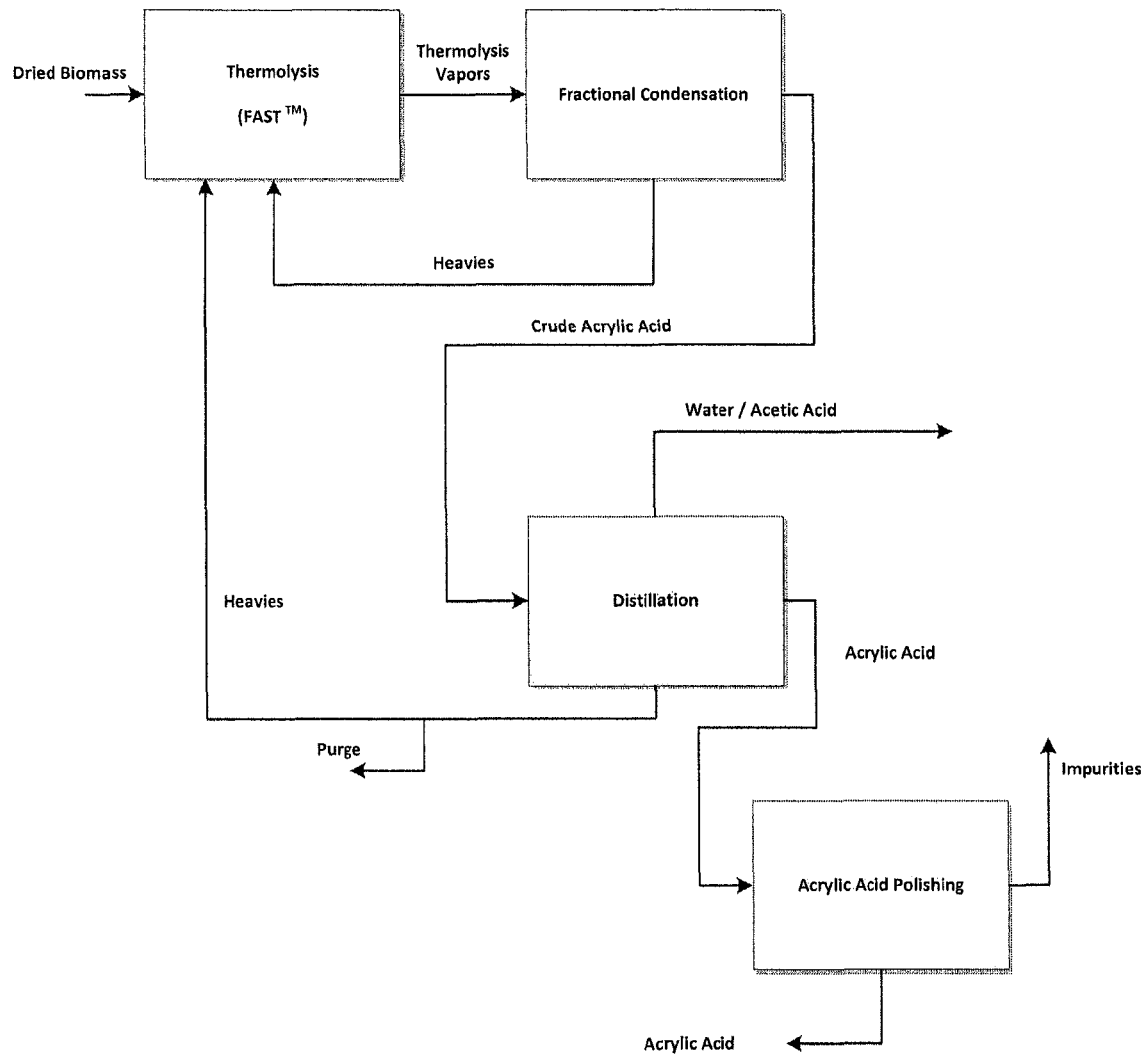
FIG. 7 is a schematic diagram of the biorefinery equipment to produce biobased acrylic acid from P3HP biomass using the FAST™ pyrolyzer.

FIG. 7 shows a schematic diagram of a commercial process for the continuous production of high purity (>99%) biobased acrylic acid from poly-3-hydroxypropionate-containing biomass. The P3HP biomass is prepared from a genetically engineered *E. coli* in a fermenter using glucose as the feed supplemented with the addition of vitamin B12. After fermentation, the biomass is either washed using centrifugation or is concentrated directly using a triple effect evaporator. The concentrated broth is then dried using either a spray dryer or a double drum dryer. Alternatively, the unwashed, centrifuged P3HP biomass can be used as the starting material for the thermolysis reactor.

The process starts with dry or wet P3HP biomass+catalyst being fed to the Fast Acting Selective Thermolysis (FAST™) reactor. The reactor temperature can be set at 250-350° C. and has a capacity to handle several hundred kilograms of dried biomass material per hour. An inert gas purge is used to assist in moving the organic vapors generated during pyrolysis along to the separation and purification equipment. The inert gas purge can be gases such as nitrogen or carbon dioxide. Optionally, steam can also be used as a process gas since water is generated by the pyrolysis reaction.

The vapor stream from the FAST™ reactor is a mixture of 90% water/organics and 10% inert vapor. Thus, unlike the production of acrylic acid from oxidation of propene where the reactor effluent is mainly a gas stream with organics present, thermolysis of P3HP biomass produces a predominantly organic vapor effluent stream. Therefore an absorber/gas compressor normally located after the reactor is not needed in the process. After the thermolysis is complete (0.25-1 hour), the spent biomass+catalyst residue exits out of the reactor to be used either as fuel in another operation or the catalyst can be reclaimed and mixed with unreacted P3HP biomass and processed over again.

After the organic vapor stream exits the reactor, it is introduced into a fractional condensation column to remove acetic acid, water as well as heavier components such as diacrylic acid from the acrylic acid. A typical fractionation condensation column for separation of high temperature acrylic acid gas mixtures is described in U.S. Pat. No. 6,646,161. Ideal gas mixtures for this type of equipment include those where there are at least two condensable components and at least one noncondensable component and where none of the components form azeotropic mixtures. The column contains separatory internals such as bubble trays, sieve trays, valve trays or dual-flow trays for the fractional condensation of the hot vapor mixture produced by the thermolysis reactor. There can be multiple cooling devices which are located at the top middle and bottom of the column. A tube-bundle or plate-type heat exchanger is also part of the column. The condensed fractions from the hot vapor mixture are removed by side take-offs from different sections of the column depending on if the liquids are low boilers (near the column top), medium boilers (middle section of column) or high boilers a.k.a heavies (lower section of column). The inert gas present exits the top of column. The column is typically operated at pressures of 0.8-3 bars and temperatures in the range of −40° C. to 450° C. FIG. 7 is a diagram showing that heavies like diacrylic acid can be recycled back to the FAST™ reactor in order to convert the diacrylic acid back to acrylic acid. Another method to convert the diacrylic acid to acrylic would be to pass the hot vapor mixture over a catalyst bed containing catalysts such as $TiO_2$, $Al_2O_3$, $SiO_2$, zeolite HZM 5 prior to introduction to the fractional condensation column (Japanese Patent No. JP03178949).

Another type of column that could be utilized for the separation of the acrylic acid vapor is a two-walled column as described in US Application No. 20120006673.

The acrylic acid mixture exiting the fractional condensation column is termed "crude" product and consists of ≤99% acrylic acid by weight. In order to reduce the concentrations of water, acetic acid and heavies even further, it can be processed using a distillation column as described in U.S. Pat. Nos. 7,332,624 and 7,179,875 and shown in FIG. 7.

Additionally a final "polishing" of the acrylic acid exiting the distillation column can be carried out in order to produce acrylic acid liquid that is >99% purity. This could include further processing steps such as a suspension crystallization step (U.S. Pat. Nos. 6,482,981 and 7,179,8750), an acid washing step followed by additional distillation or an ion exchange step to remove impurities such as nitrogen-containing compounds (amides, amines, pyridines).

At each process step, an inhibitor can be added to the acrylic acid to prevent polymerization during processing. The inhibitors include single compounds such as the methyl ester of hydroquinone (MEHQ), phenothiazine (PZT), 4-hydroxy-2,2,6,6-tetramethyl-1-piperidinyloxy (HTEMPO), salicylate, copper salts or mixtures of these.

Example 6. Preparation of N-Butyl Acrylate from Biobased Acrylic Acid

This example illustrates the process of direct esterification with n-butanol of biobased acrylic acid (>99%) as produced in Example 5 from P3HP biomass. To a continuously fed, stirred-tank reactor containing a cation exchange resin-type catalyst (Amberlyst™ 46, Rohm Haas/Dow), a mixture of n-butanol and biobased acrylic acid at a 1:1 mass ratio is added. The reactor is heated to and maintained at a constant temperature of 90° C. As the esterification reaction proceeds, a distillation column attached to the reactor separates generated water from the n-butyl acrylate. Any residual n-butanol and acrylic acid are then separated from the n-butyl acrylate collected by an additional fractional distillation step.

Example 7. Preparation of Butyl Acrylate Directly from Biomass with Poly-3-Hydroxypropionate (P3HP) by Telescopic Synthesis This example describes a method for producing biobased butyl acrylate directly from biomass containing P3HP polymer. Two grams of washed/dried biomass containing P3HP (~60% by weight P3HP within the biomass) was added to a 250 ml single neck round bottom flask equipped with a magnetic stir bar. 100 ml of n-butanol (>99.4%, Sigma Aldrich) and 0.2-8 g of transesterification/dehydration catalyst (95-98% sulfuric acid, Sigma Aldrich), were added to the flask. Note that the n-butanol was not dried over molecular sieves prior to use. The flask, equipped with a Dean-Stark trap (Vtrap=35 ml), was then heated to reflux for 21 hours with stirring. After the reaction was complete, the mixture was left to cool to room temperature. 200 µl of the reaction mixture was diluted with 1300 µl of MeCN and 300 µl of $H_2O$ (dilution factor=7.5-9), filtered, and the amount of n-butyl acrylate produced was determined via Reverse phase HPLC analysis using a Shimadzu Moduluar HPLC system having an RI detector. The HPLC column used and run conditions were as follows: Phenomenex Reverse Phase HPLC Column (Luna® 5 µm C18(2) 100 Å, 150×2 mm, Stationary Phase: C18 with TMS end capping, Cat. No. 00F-4252-B0), C18 SecurityGuard cartridge (2×4 mm, Phenomenex Cat. No. AJ0-4286, KJ0-4282 holder), 40° C. column temperature, 5 µl injection volume, mobile phases $H_2O$ and MeCN, 0.5 ml/min flow rate, 210 nm detection, 0.0 to 6.0 min: 30% MeCN/$H_2O$ isocratic; 6.0 to 8.0 min: 30 to 60% MeCN/$H_2O$ gradient; 8.0 to 10.0 min: 60% MeCN/$H_2O$ isocratic; 10.0 to 11.0 min: 60% to 30% MeCN/$H_2O$ gradient; 11.0 to 16.0 min: 30% MeCN/$H_2O$ isocratic.

Table 5 shows the results of the percent yield of butyl acrylate versus the weight $H_2SO_4$ catalyst added. The highest yield at 90% was observed when a weight ratio of catalyst/biomass+P3HP was equal to 4. It was found that when equimoles of catalyst to polymer were used, the reaction only produced low yield butyl acrylate and so other undesirable side products such as butene.

TABLE 5

Summary of HPLC data for direct conversion of dry biomass + P3HP to butyl acrylate. Catalyst was $H_2SO_4$ (99.4% Sigma Aldrich). n-Butanol (95 = 98% Sigma Aldrich) was added to all sample in excess at 100 ml total volume.

| Sample ID | Wt. of Biomass + P3HP (g) | % P3HP in Biomass | Wt. P3HP (g) | Wt. of Catalyst (g) | Ratio of Catalyst/ Biomass + P3HP | Conversion/ Yield of n-Butyl Acrylate (%) |
|---|---|---|---|---|---|---|
| 1 | 2 | 60 | 1.2 | 0.25 | 0.13 | 2.7 |
| 2 | 2 | 60 | 1.2 | 0.5 | 0.25 | 14.1 |
| 3 | 2 | 60 | 1.2 | 1 | 0.50 | 19.5 |
| 4 | 2 | 60 | 1.2 | 2 | 1.00 | 23.1 |
| 5 | 2 | 60 | 1.2 | 4 | 2.00 | 63.0 |
| 6 | 2 | 60 | 1.2 | 8 | 4.00 | 90.4 |

The biobased content of the prepared butyl acrylates listed in Table 5 would be approximately 42% due to the fact that petroleum based n-butanol was used. Alternatively, biobased n-butanol produced as described in U.S. Pat. No. 8,119,367 and US Patent applications 2010/0330633, 2011/0087000 and 2011/0159558 can be utilized in the telescopic synthesis reaction. In this case, the butyl acrylate produced would have a biobased content of 100%. Several other compounds were screened as potential catalysts for direct conversion of P3HP to butyl acrylate. These included p-toluene sulphonic acid, methyl sulphonic acid, zinc oxide (ZnO), zinc chloride ($ZnCl_2$), iron chloride ($FeCl_3$), silica, alumina, titanium dioxide, phosphoric acid ($H_3PO_4$), kaolinite and the immobilized sulphonic acid catalyst AMBERLYST™15 resin acid catalyst. Sulfuric acid was also added as a control. The samples were prepared as described above with the catalyst/P3HP ratio being 3.3/1 (4 g/1.2 g). Table 6 below shows the yield of butyl acrylate from biomass+P3HP mixed with these various catalysts.

TABLE 6

Summary of HPLC data for direct conversion of washed/dried biomass + P3HP to butyl acrylate using various catalysts. 4 g catalyst was mixed with 2 g of biomass + P3HP (1.2 g P3HP). n-Butanol (95 = 98% Sigma Aldrich) was added to all sample in excess at 100 ml total volume.

| Sample ID | Catalyst | Wt. Catalyst (g) | Wt. P3HP (g) | Conversion/Yield of n-Butyl Acrylate (%) |
|---|---|---|---|---|
| 1 | $H_3PO_4$ | 4 | 1.2 | 0.9 |
| 2 | $H_2SO_4$ | 4 | 1.2 | 63.0 |
| 3 | methane sulphonic acid | 4 | 1.2 | 5.8 |
| 4 | p-toluene sulphonic acid | 4 | 1.2 | 24.8 |
| 5 | AMBERLYST ™ 15 | 4 | 1.2 | 1.4 |
| 6 | $ZnCl_2$ | 4 | 1.2 | 7.7 |
| 7 | ZnO | 4 |  | 17.2 |
| 8 | $FeCl_3$ | 4 | 1.2 | 18.2 |
| 9 | kaolinite | 4 | 1.2 | 0.5 |
| 10 | $TiO_2$ | 4 | 1.2 | 0.5 |
| 11 | $Al_2O_3$ | 4 | 1.2 | 1.3 |
| 12 | $SiO_2$ | 4 | 1.2 | 1.4 |
| 13 | dibutyl tin laurate | 4 | 1.2 | 44.6 |

Within the reaction sequence, three events must occur in order for the catalyst to be effective: biomass cells containing the P3HP are opened, transesterification of the P3HP with n-butanol to form n-butyl 3-hydroxypropionate, followed by dehydration of the n-butyl 3-hydroxypropionate to form the n-butyl acrylate. The data in Table 6 shows that the most effective catalyst for converting P3HP to butyl acrylate was sulfuric acid followed by dibutyl tin laurate, p-toluene sulphonic acid, iron chloride and zinc oxide.

Example 8. Preparation of Biobased Polyacrylic Acid Superabsorbent Polymer

To a 3 liter jacketed reaction vessel 250 g of distilled-deionized (DI) water, 295 g of biobased acrylic acid monomer (>99%) prepared as described in Example 5 and 0.26 g of the multifunctional monomer trimethylolpropane triacrylate (TMPTA, Sigma Aldrich) are added. Water at T=25° C. is circulated through the jacketed vessel using a temperature-controlled water bath. To the monomer-water mixture in the reaction vessel, 580 ml of 5N sodium hydroxide solution is also added. A mechanical stirrer is placed into the vessel and then a multiport lid is then clamped on top of the reactor. A thermometer, nitrogen purge inlet and outlet lines are connected to three of the reactor ports. The stirrer is started and the nitrogen purge line is submerged in the liquid. After 15 min, the nitrogen purge line is pulled out of the liquid and allowed to purge the space above the liquid during the remainder of the reaction. Three milliliters of a 0.098 g/ml solution of sodium persulfate free radical initiator (Sigma Aldrich) and a small aliquot of a 0.0021 g/ml L-ascorbic acid (Sigma Aldrich) solution are added to the reaction vessel through the remaining port using a microsyringe. The polymerization reaction proceeds at 25° C. for 30 minutes, then 40° C. for 30 min, and finally 50° C. for 1 hour. Total synthesis time is 2 hours. At the end of the reaction, the stirrer is stopped and removed. The circulating water bath is then set back to 25° C. and the vessel allowed to cool. Once the vessel is cooled, the liquids are filtered off and the polyacrylate gel is collected then dried in a vacuum oven.

Example 9. Generation of Acrylic Acid from Sodium Hydroxyisobutyrate (Na-HIB)

In this example, pyrolysis-GC-MS was carried at 400° C., 500° C. and 700° C. on a pure sodium hydroxyisobutyrate (Na-HIB) powder (Sigma Aldrich) in order to identify the thermal degradation compounds generated. The generation of acrylate compounds such as methacrylic acid and methyl methacrylate were particularly of interest. In order to identify the monomer compounds generated by thermal degradation at various temperatures, an Agilent 6890 GC-MS equipped with a Scientific Glass Engineering PYROJECTOR™ II pyrolysis unit was used. For this technique, a sample was weighed into a cleaned quartz glass tube and loaded into the pyrolyzer. When the pyrolyzer and GC-MS were started, the glass tube was automatically placed into the pyrolyzer which has been set to a specific temperature. The sample was held in the pyrolyzer for 1-2 minutes while volatiles were released by the sample. The volatiles were then swept using helium gas into the GC column where they condense onto the column which was set at a lower temperature relative to the pyrolyzer. Once the pyrolysis was completed, the glass tube was ejected from the pyrolyzer and the GC column was heated at a certain rate in order to elute the volatiles released from the sample. The volatile compounds were then swept using helium gas into an electro ionization/mass spectral detector (mass range 10-700 daltons) for identification and/or quantitation.

For the following example, approximately 1 mg of Na-HIB compound was weighed into a cleaned quartz glass tube using a microbalance. The glass tube was then loaded into the pyrolyzer. The pyrolyzer was programmed to heat to temperatures 400° C., 500° C. and 700° C. for a duration of 1 minute. The GC column used in the examples was a Restek MS-1 (30 m×0.25 mm with 1 μm phase coating). The GC oven was then programmed to heat from 35° C. to 325° C. at 15° C./min having an initial 2 min. hold at 35° C. Peaks showing in the chromatogram were identified by the best probability match to spectra from a NIST mass spectral library.

Figure 8:
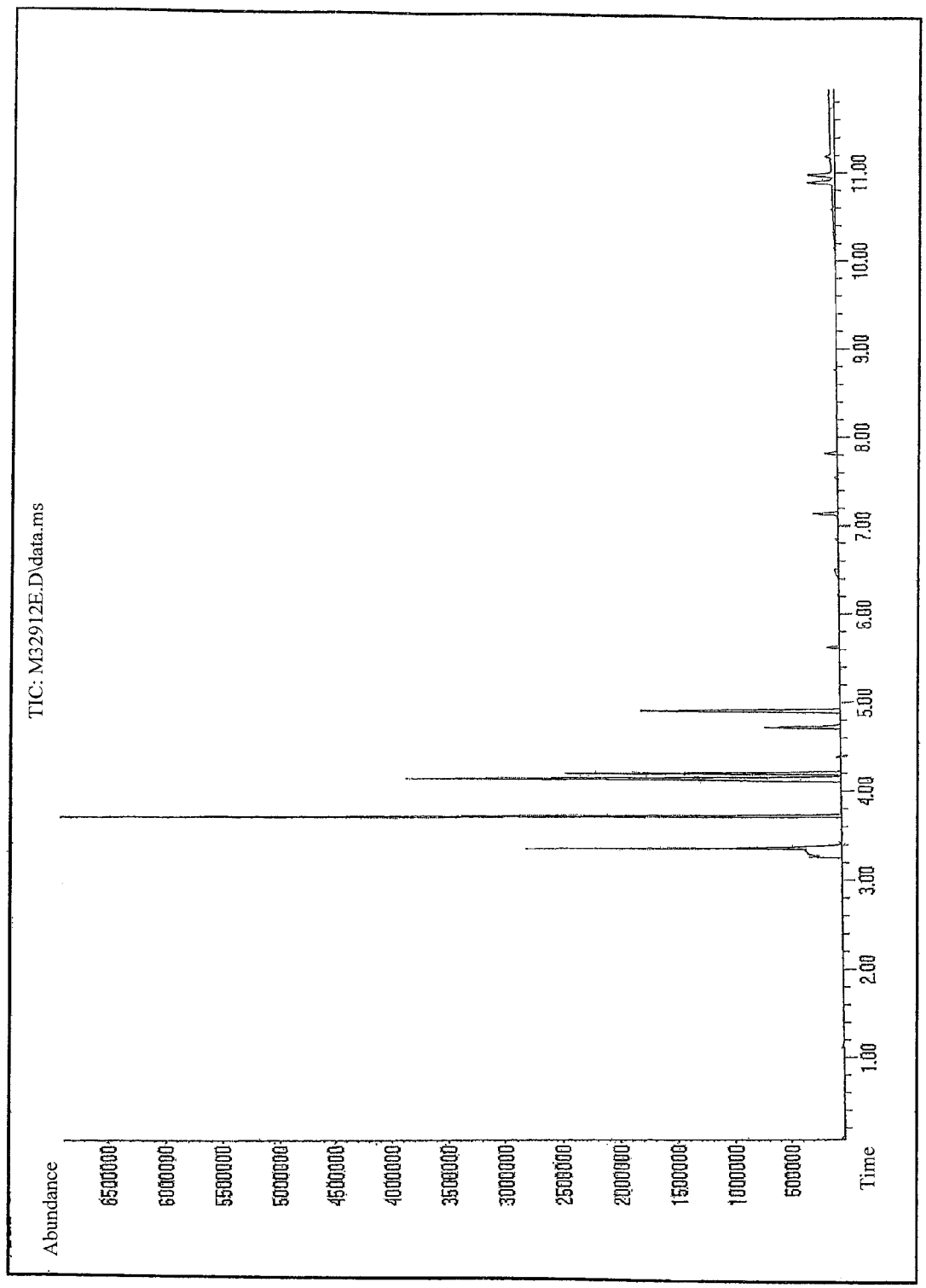
FIG. 8 is a total ion chromatogram plot of the thermal degradation products from sodium-hydroxyisobutyrate pyrolyzed at 400° C. for 1 minute
Figure 9:
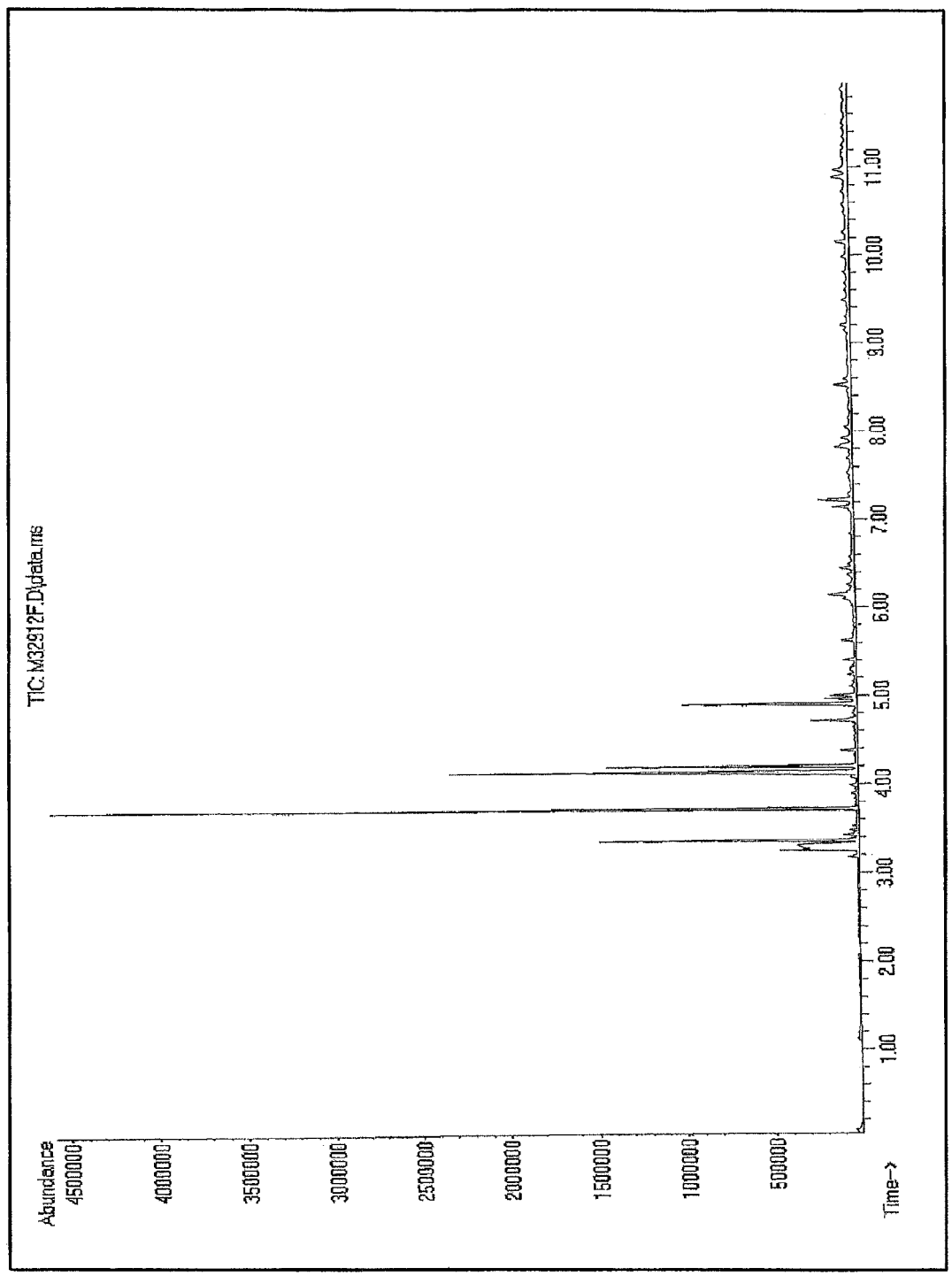
FIG. 9 is a total ion chromatogram plot of the thermal degradation products from sodium-hydroxyisobutyrate pyrolyzed at 500° C.
Figure 10:
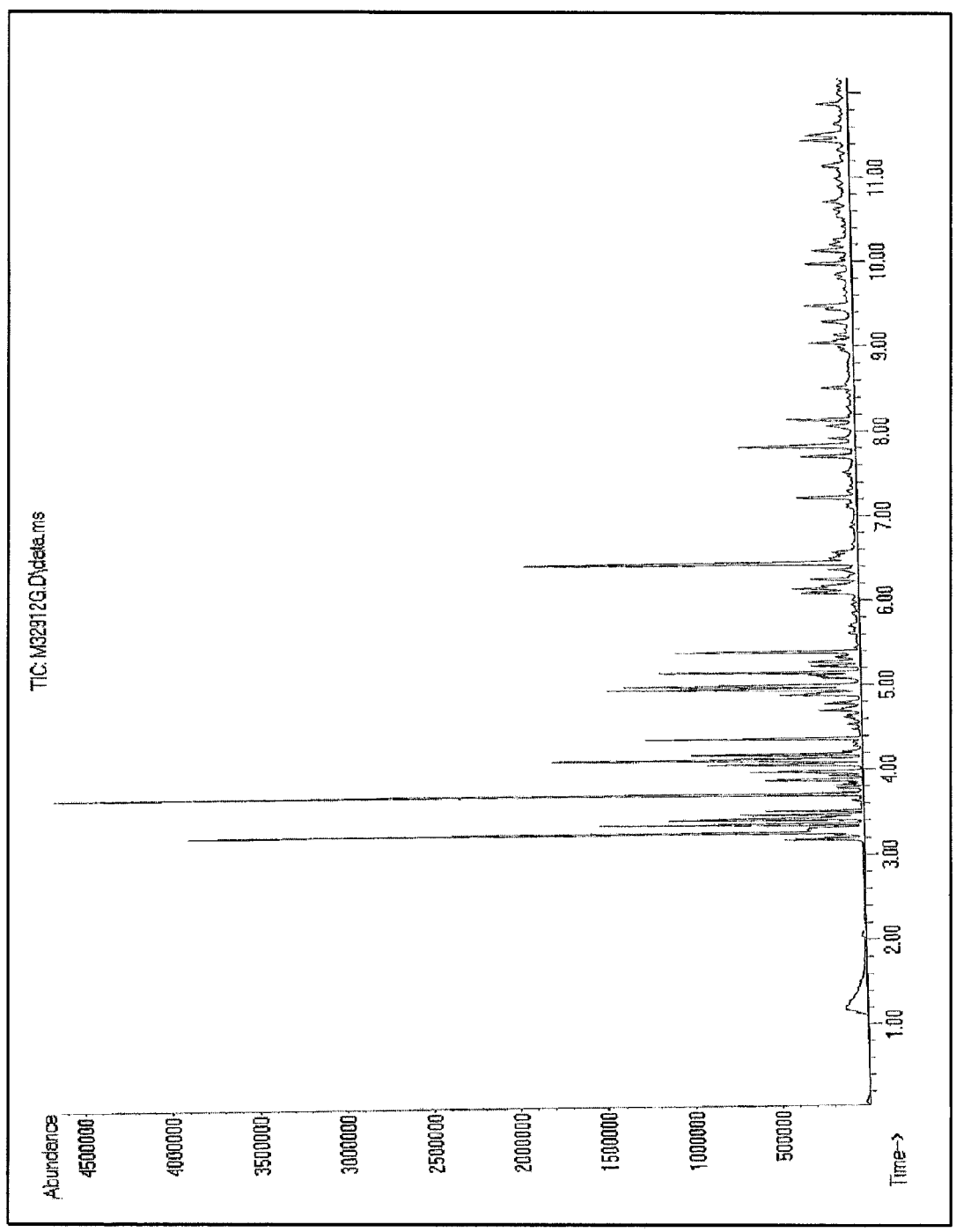
FIG. 10 Total ion chromatogram plot of the thermal degradation products for sodium-hydroxyisobutyrate pyrolyzed at 700° C.
Figure 11:
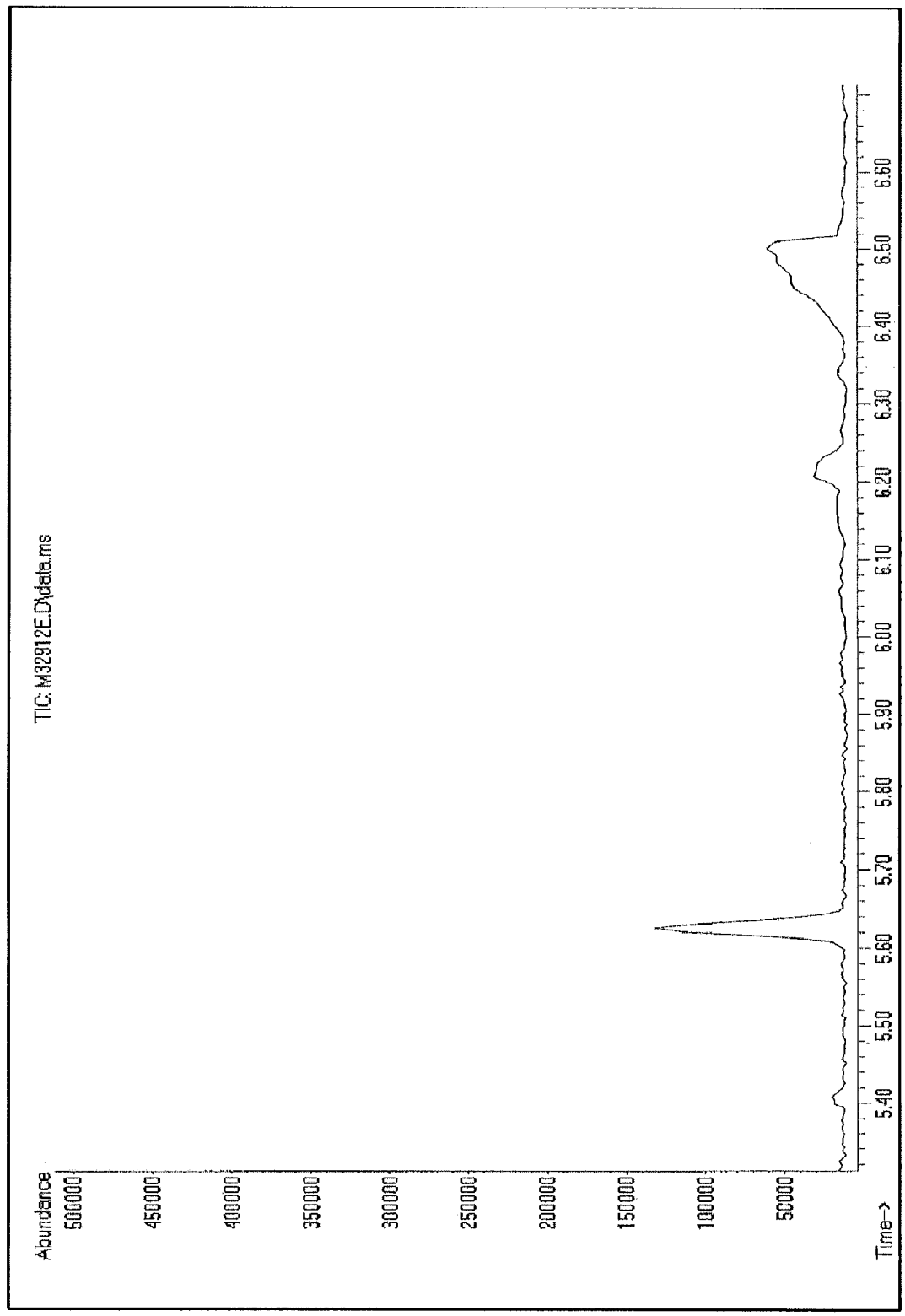
FIG. 11 is an expanded view of Total ion chromatogram from pyrolysis of sodium-hydroxybutyrate at 400° C. showing peaks for methylmethacrylate (@5.63 min and methacrylic acid @6.49 min.
Figure 12:
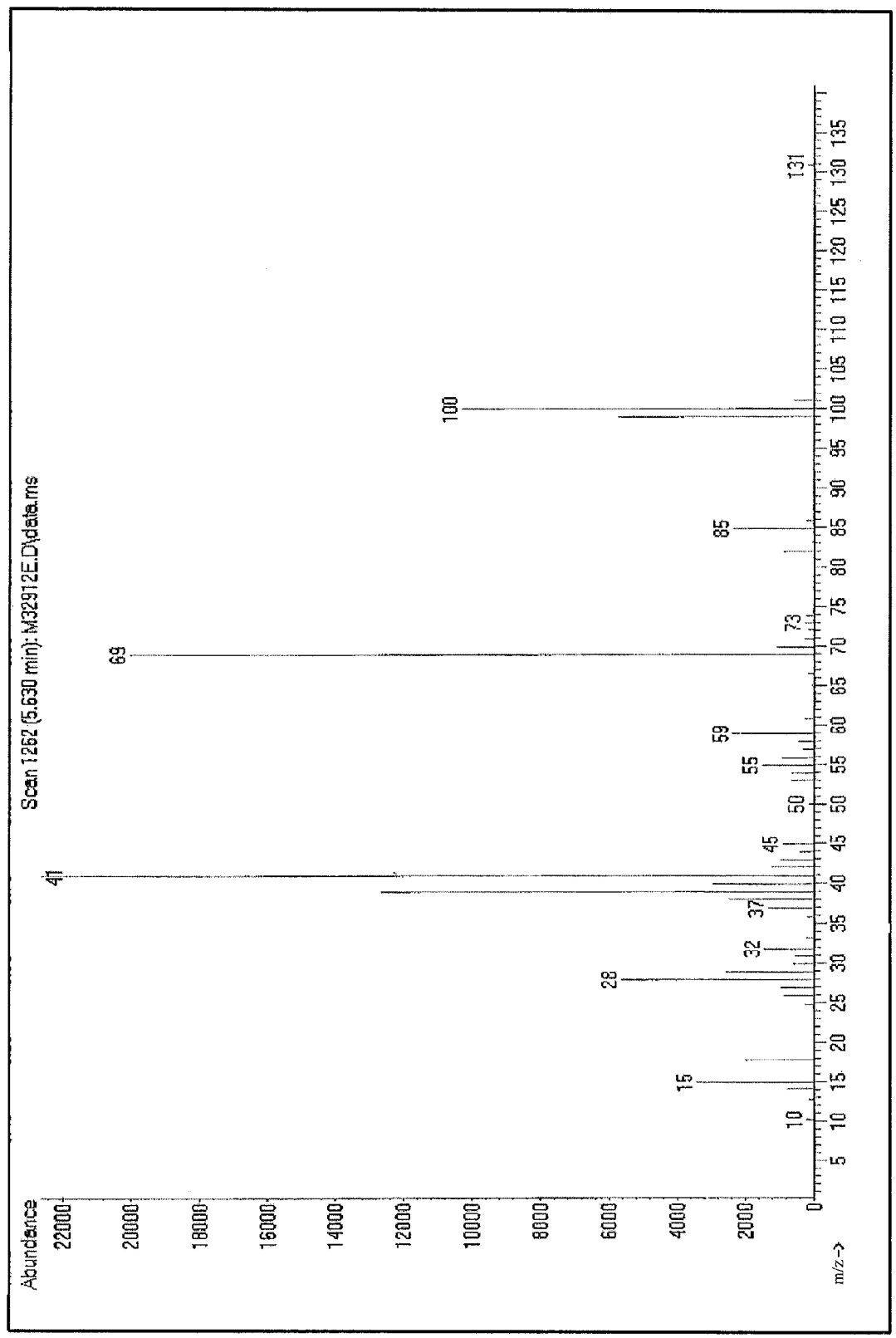
FIG. 12 is a mass spectrum of chromatogram peak @5.63 min from FIG. 11 (top). Also shown is the NIST spectral library match to methyl methacrylate (bottom).
Figure 12:
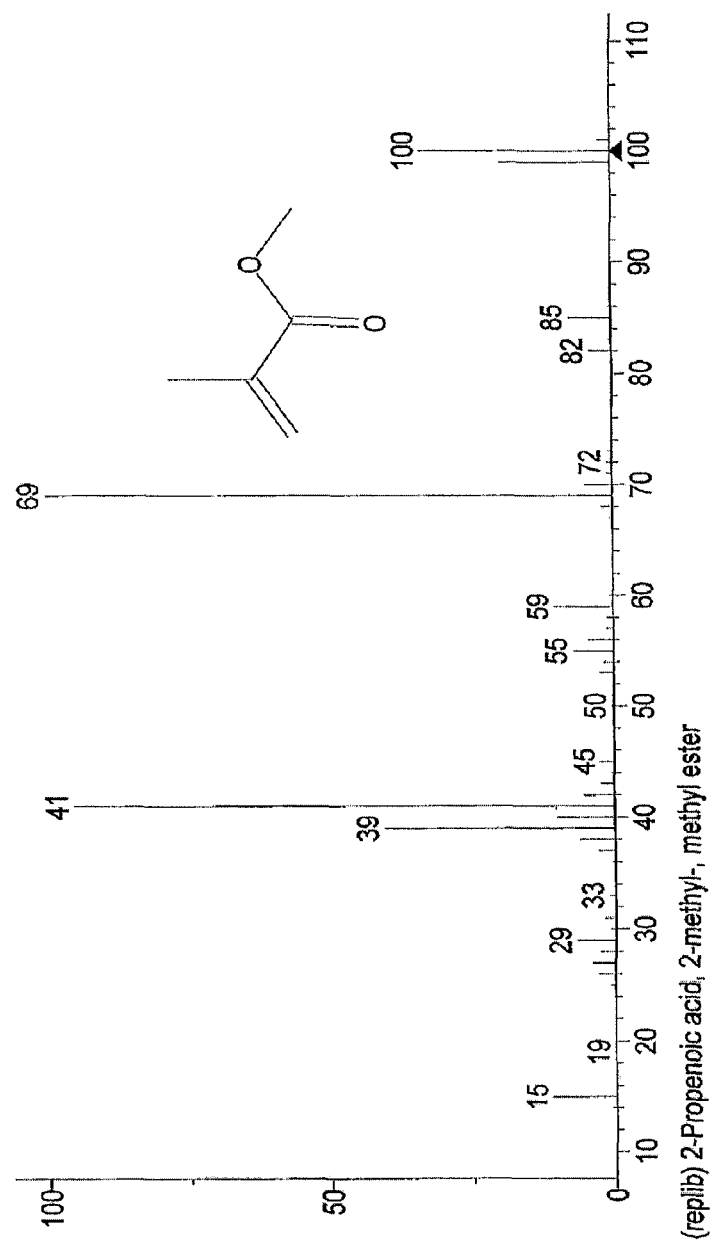
Figure 13:
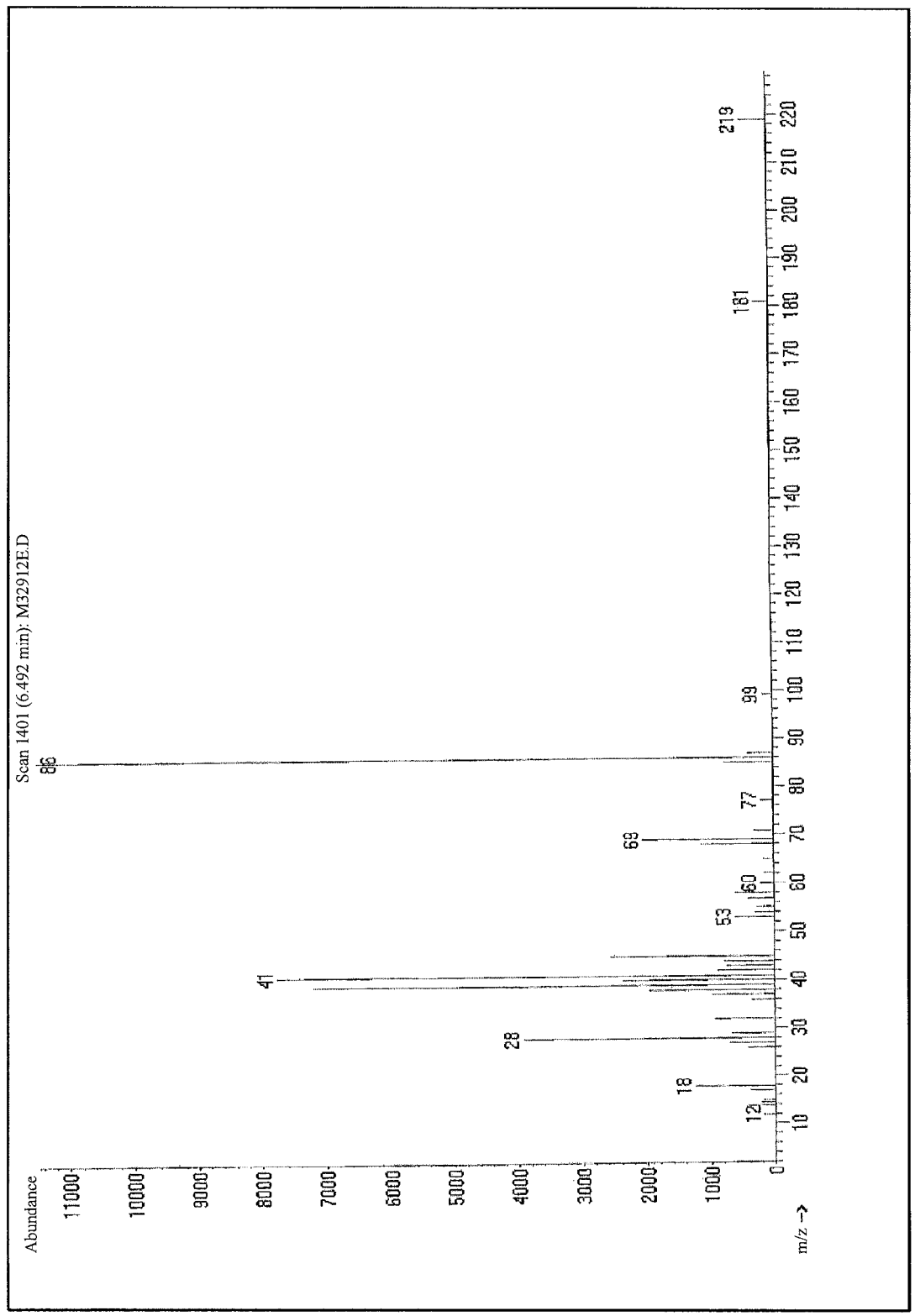
FIG. 13 is a mass spectrum of chromatogram peak @ 6.49 min from FIG. 11 (top). Also shown is the NIST spectral library match to methacrylic acid (bottom).
Figure 13:
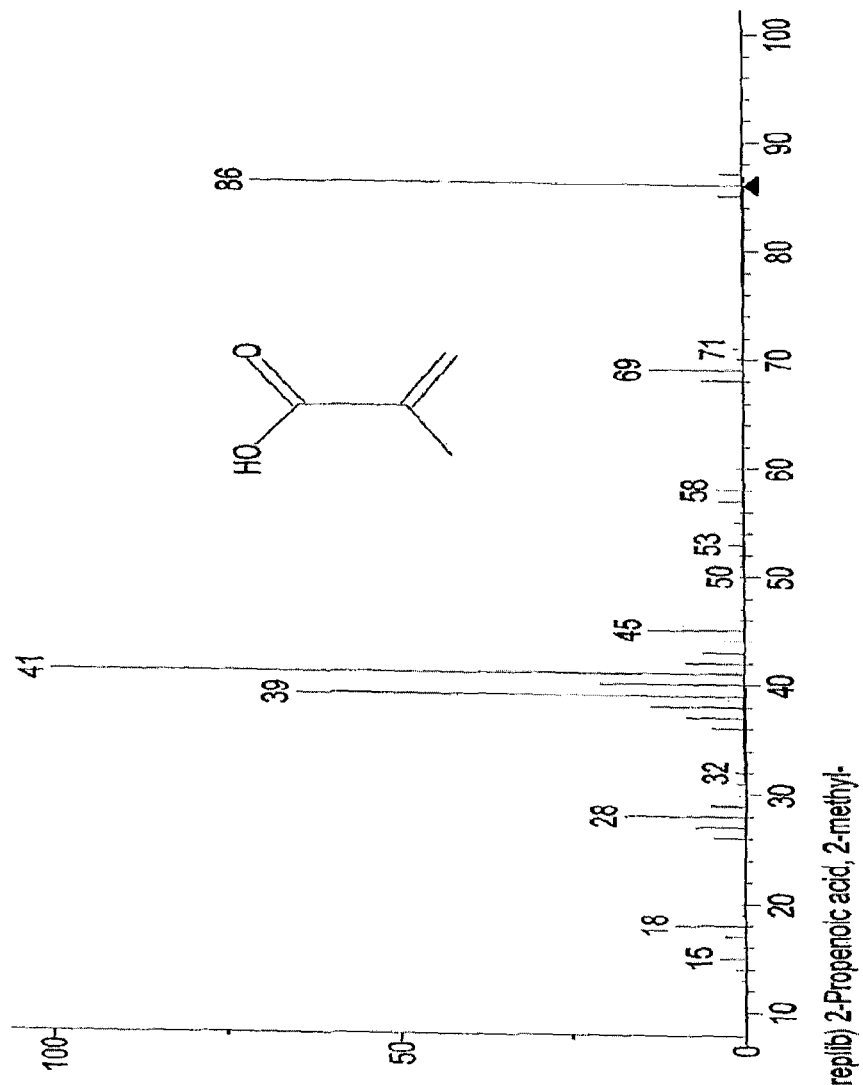
Figure 14:
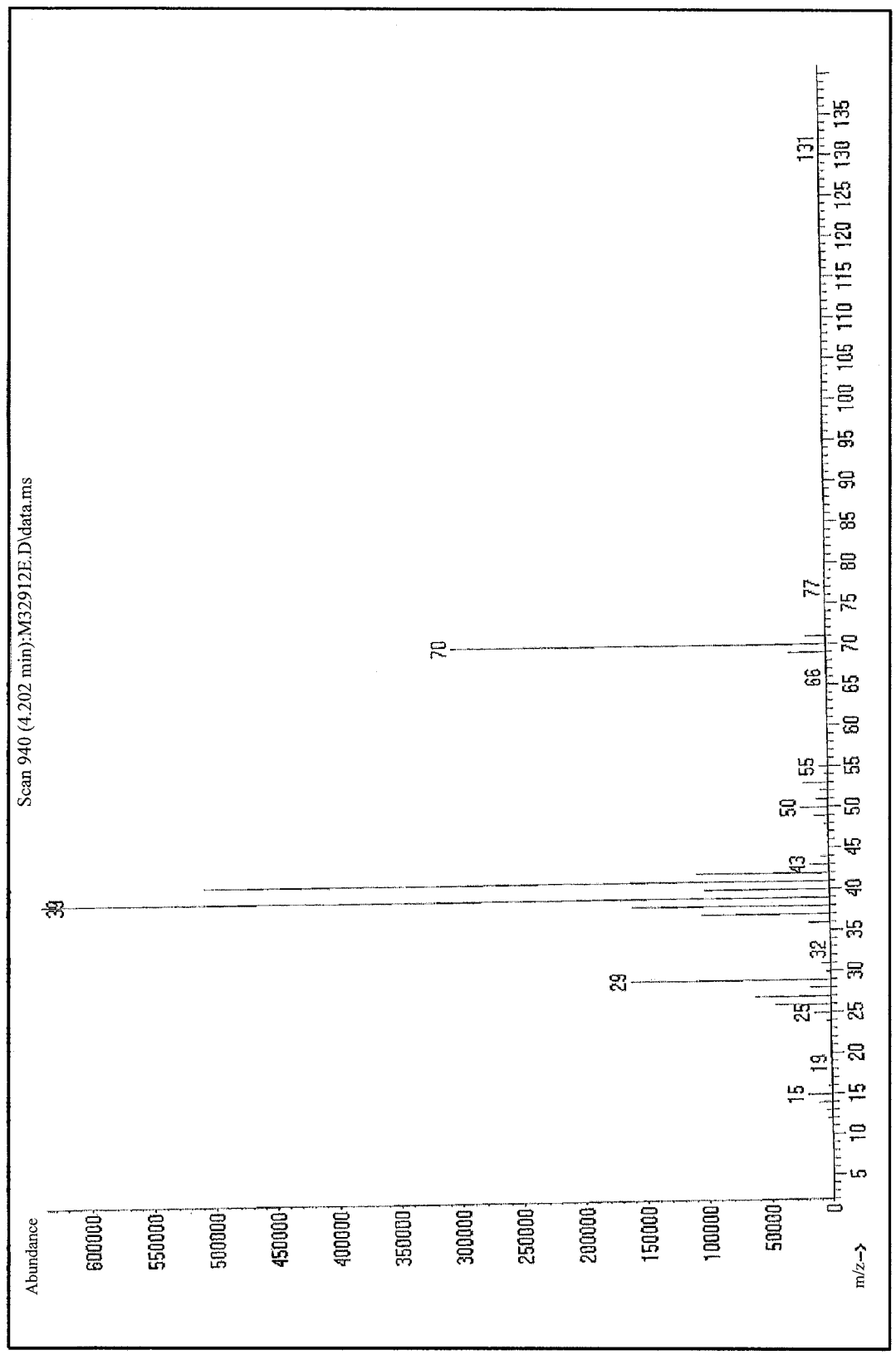
FIG. 14 is a mass spectrum chromatogram peak @4.2 min from FIG. 11 (top). Also shown is the NIST spectral library match to methacrylaldehyde or methacrolein (bottom).
Figure 14:
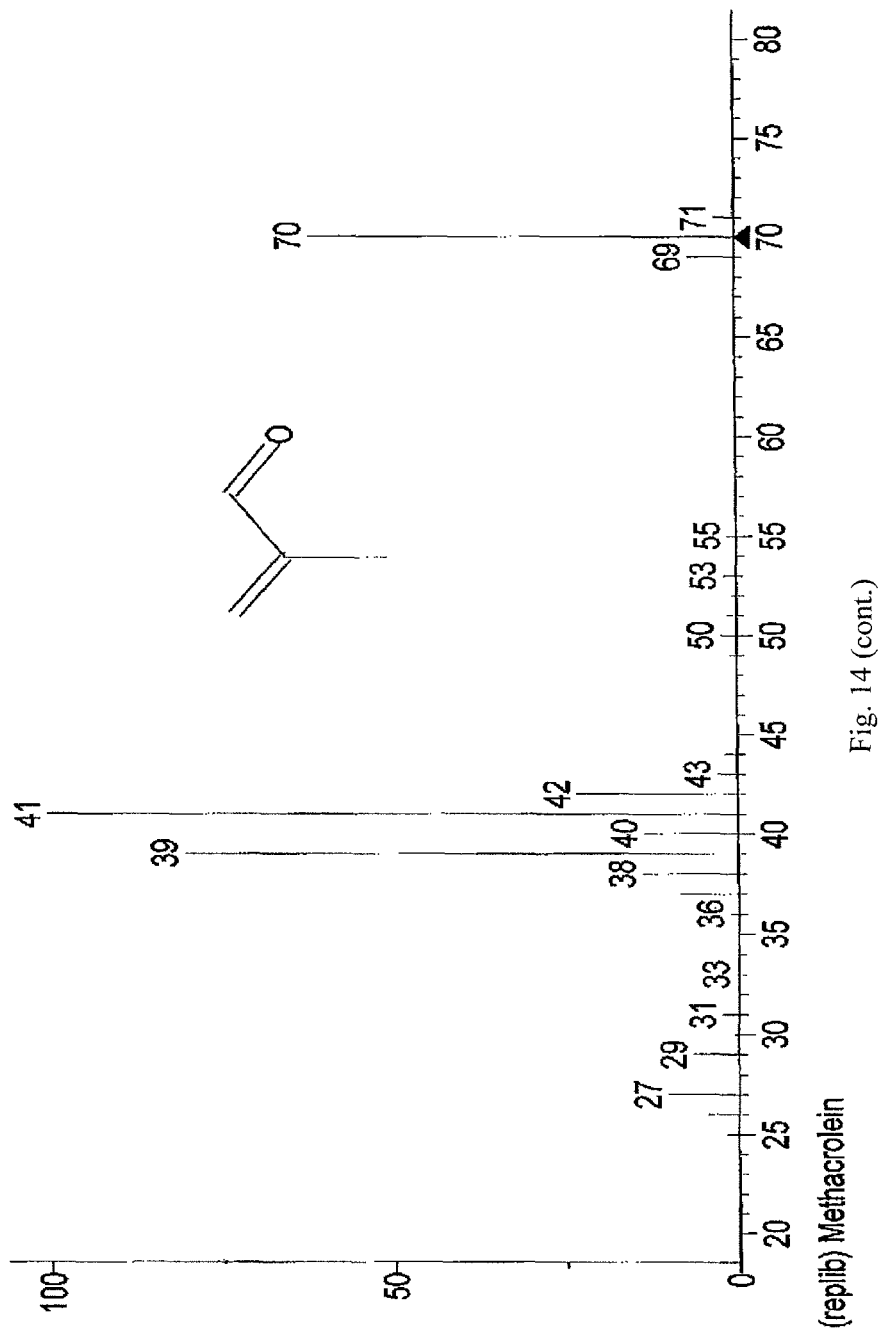

FIGS. 8-10 show the Total Ion Chromatograms plots for the pyrolysis of Na-HIB at 400° C., 500° C. and 700° C. while Table 7 summarizes the pyrolysis degradation products identified by mass spectroscopy. Both methyl methacrylate at a retention time of 5.62 minutes and methacrylic acid at a retention time of 6.50 minutes were identified as degradation products from the pyrolysis of Na-HIB at 400° C. and 500° C. FIG. 11 shows an expanded view of these chromatogram peaks for the pyrolysis at 400° C. while FIGS. 12 and 13 show the mass spectrum and mass spectral library matches. Only a very small peak for methyl methacrylate was detected at the highest pyrolysis temperature of 700° C. No methacrylic acid was detected at the 700° C. pyrolysis temperature. The total peak area % for these compounds (~1-2%) was found to decrease as the pyrolysis temperature increased. Maximization of acrylate yield using pyrolysis either of the pure Na-HIB or of biomass+PHIB would likely occur at temperatures in 250-350° C. range. Also detected at all pyrolysis temperatures was the acrylate compound methacrolein or methacrylaldehyde which had a retention time of 4.20 min. FIG. 14 shows the mass spectrum and NIST spectral library match for this peak identifying the compound as methacrolein. It's peak area percent was measured to be in the 9-11%. The peak area for this compound was also found to decrease as the pyrolysis temperature increased.

TABLE 7

Summary of degradation products detected by GC-MS from pyrolysis of sodium-hydroxyisobutyrate at 400° C., 500° C. and 700° C. An X in the pyrolysis temperature column indicates the particular compound identified as a degradation product.

| Compound Detected | GC-MS Pyrolysis Temperature | | |
|---|---|---|---|
| | 400° C. | 500° C. | 700° C. |
| 1-butene | | X | X |
| 2-butene | | X | X |
| 1-propanol | X | X | X |
| 1,3-cyclopentadiene | | X | X |
| 1,3-pentadiene | | | X |
| 1,4-pentadiene | | | X |
| 2-butanone | | X | X |
| 2-buten-1-ol | X | X | X |
| 2-methyl-2-pentenal | X | X | |
| 2,4-hexadiene | | X | |
| 3-pentanone | | X | X |
| Benzene | | | X |
| Toluene | | | X |
| Xylene | | | X |
| Carbon dioxide | | X | X |
| Ethane | | X | X |
| Formaldehyde | X | X | X |
| Water | X | X | X |
| Isobutyl alcohol | X | X | |
| Isobutylene | | | X |
| Methacrolein | X | X | X |
| Methacrylic acid | X | X | |
| Methyl methacrylate | X | X | X |
| Methanol | X | X | X |
| N-propyl-methacrylate | X | | |
| Propanal | X | X | X |
| Propanal-2-methyl | X | X | |
| Propene | X | X | X |

Production of 3-hydroxyisobutyrate (HIB) or poly-3-hydroxyisobutyrate (PHIB) in biomass has been described in US Patent Application No. 20100068773 and 20100291644. Alternatively these could be used as the starting material for production of methacrylic acid and methyl methacrylate by pyrolysis of biomass containing HIB or PHIB.

Example 10. Generation of Biobased Acrylic Acid from Pyrolysis of P3HP Biomass with the Addition of a Volatile Heat Transfer Fluid In this example, a heat transfer fluid which boils close to the pyrolysis temperature (at atmospheric pressure) is added to washed, dried and ground P3HP biomass in order to facilitate conversion of the P3HP to acrylic acid during pyrolysis. A mixture containing 153 g of WDG P3HP biomass and 53.7 g of octanoic acid ($T_{boil}$=239° C.) was prepared and then loaded into the pyrolysis apparatus described in Example 4. The mixture was then heated under nitrogen to a pyrolysis temperature of 275° C. for a period of 1 hour and the volatiles collected using a water-cooled condenser. The weight of condensed volatiles collected was 131.5 g total. For comparative purposes, a similar experiment was carried out using 156.8 g of WDG P3HP biomass but without the addition of the heat transfer fluid (octanoic acid). In this experiment, the weight of condensed volatiles collected was 64.8 g total. The results showed that the ratio of the weight of condensed volatiles collected/initial weight of the starting reactants was 23% higher when the heat transfer fluid, octanoic acid, was added prior to the start of pyrolysis. In addition, analysis of the condensate from pyrolysis of P3HP biomass+octanoic acid mixture showed that all of the octanoic acid had been released during pyrolysis and recovered. To separate the acrylic acid from the heat transfer fluid in the condensate, an additional step such as distillation, solvent extraction or even filtration would be implemented. Additional acrylic acid purification steps may also be necessary. The heat transfer fluid itself once isolated from the condensate can also be purified, dried and then used in subsequent pyrolysis runs. Other volatile heat transfer fluids which could also be utilized include gamma-butyrolactone, hexanoic acid, heptanoic acid, nonanoic acid, decanoic acid or diphenyl/biphenyl constituted vapor/liquid phase, heat transfer fluids supplied by Solutia Inc. such as THERMINOL® VP-1 heat transfer fluid and THERMINOL® VP-3. The boiling points of these heat transfer fluids ranges from 200-270° C. A catalyst such as those described in Examples 2 and 3 could also be added with the P3HP biomass and heat transfer fluid.

Example 11. Generation of Biobased Acrylic Acid from Pyrolysis of P3HP Biomass with the Addition of a Nonvolatile Heat Transfer Fluid In this example, a heat transfer fluid that does not boil off during pyrolysis but rather remains with the biomass until the completion of pyrolysis is added to the P3HP biomass prior to pyrolysis. A mixture of 100 g of washed, dried and ground P3HP biomass, 2 g of catalyst (see Examples 2 and 3) and 30-50 g of a nonvolatile heat transfer fluid is prepared. The mixture is then pyrolyzed at 250-275° C. in an apparatus as described in Example 4. The volatiles consisting of acrylic acid, water and biomass impurities are collected using a water-cooled condenser. An alternate approach is to create a slurry or a suspension of the P3HP biomass+catalyst in the heat transfer fluid and pyrolyze the mixture using either a batch or a continuous process as described in Example 5. After pyrolysis, the biomass suspension remaining is filtered and the heat transfer fluid recovered to be used in subsequent pyrolysis runs. Heat transfer fluids suitable for use in the above process include THERMINOL® heat transfer fluid 50, THERMINOL® heat transfer fluid 66 or THERMINOL® heat transfer fluid 72 (Solutia Inc.), MARLOTHERM® SH heat transfer fluid or heat transfer fluid LH (Sasol), THERMOFLO A® heat transfer fluid (Chem Group), PARATHERM® MR heat transfer fluid or heat transfer fluid PARATHERM® R (Paratherm Corp.) or products from Dow such as DOWFAX® heat transfer fluid, DOWTHERM® heat transfer fluid, SYLTHERM® heat transfer fluid or DOWCAL® heat transfer fluid.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A process for production of a biobased acrylic acid product, comprising:
   a) combining a genetically engineered host biomass comprising poly-3-hydroxypropionate, a heat transfer fluid having a boiling temperature, and optionally a catalyst to obtain a biomass mixture; and
   b) heating the biomass mixture at a heating temperature to convert the poly-3-hydroxypropionate to an acrylic acid product;
   wherein a yield of the acrylic acid product is at least 80% and the biobased carbon content of the acrylic acid product is at least 90%.

2. The process of claim 1, wherein the yield of the acrylic acid product is at least 85% and the biobased carbon content of the acrylic acid product is at least 95%.

3. The process of claim 1, wherein a yield of the acrylic acid product is at least 80% and the biobased carbon content of the acrylic acid product is at least 98%.

4. The process of claim 1, wherein the process further includes an initial step of culturing the genetically engineered host with a renewable feedstock to produce a poly-3-hydroxypropionate.

5. The process of claim 4, wherein a source of the renewable feedstock is selected from glucose, fructose, sucrose, arabinose, maltose, lactose, xylose, ethanol, methanol, glycerol, fatty acids, vegetable oils, and biomass derived synthesis gas or a combination thereof.

6. The process of claim 1, wherein the genetically engineered host is a bacteria, yeast, fungi, algae, cyanobacteria, or a mixture of any two or more thereof.

7. The process of claim 6, wherein the genetically engineered host is bacteria.

8. The process of claim 7, wherein the bacteria is selected from *Escherichia coli, Alcaligenes eutrophus* (renamed as *Ralstonia eutropha*), *Bacillus* spp., *Alcaligenes latus, Azotobacter, Aeromonas, Comamonas, Pseudomonads*), *Pseudomonas, Ralstonia, Klebsiella*), *Synechococcus* sp PCC7002, *Synechococcus* sp. PCC 7942, *Synechocystis* sp. PCC 6803, *Thermosynechococcus elongatus* BP-I, *Chlorobium tepidum, Chloroflexusauranticus, Chromatium tepidum* and *Chromatium vinosum Rhodospirillum rubrum, Rhodobacter capsulatus*, and *Rhodopseudomonas palustris*.

9. The process of claim 6, wherein the genetically engineered host is algae.

10. The process of claim 1, wherein the heating temperature is from 100° C. to 350° C.

11. The process of claim 1, wherein the boiling temperature of the heat transfer fluid is above the heating temperature.

12. The process of claim 11, further including the step of recovering the heat transfer fluid from the biomass mixture.

13. The process of claim 1, wherein the catalyst is sodium hydrogen sulfate or sulfuric acid or phosphoric acid.

14. The process of claim 13, wherein the weight percent of catalyst is in the range of about 4% to about 50%.

15. The process of claim 1, wherein heating reduces the water content of the biomass to about 5 wt %, or less.

16. The process of claim 1, wherein the heating temperature is from about 200° C. to about 350° C.

17. The process of claim 1, wherein the heating is performed for a time period from about 30 seconds to about 5 minutes or from about 5 minutes to about 2 hours.

18. The process of claim 1, further comprising recovering the acrylic acid product.

19. The process of claim 1, wherein the acrylic acid product comprises less than 5% by weight of side products.

20. The process of claim 1, wherein the genetically engineered host is from a recombinant host having a poly-3-hydroxypropionate pathway,
wherein the host has stably incorporated one or more genes encoding one or more enzymes selected from vicinal diol dehydratase, aldehyde dehydrogenase, 1,3-propanediol oxidoreductase, glycerol-3-phosphate dehydrogenase and glycerol-3-phosphatase.

21. The process of claim 1, wherein the weight % of the catalyst is in the range of about 4% to about 50%, and the heating is at about 250° C.

22. The process of claim 1, wherein the catalyst is about 4% by weight calcium hydroxide and the heating is at a temperature of 250° C.

23. The process of claim 1, wherein the yield of acrylic acid product is about 85% by weight or greater based on one gram of an acrylic acid in the acrylic acid product per gram of poly-3-hydroxypropionate.

24. A process for production of a biobased butyl acrylic acid ester product, comprising
a) combining a genetically engineered host biomass comprising poly-3-hydroxypropionate, n-butanol and a catalyst to produce a biomass mixture;
b) heating the biomass mixture with the n-butanol and catalyst to reflux for 15-24 hours; and
c) converting the poly-3-hydroxypropionate to a butyl acrylic acid ester product;
wherein a yield of the acrylic acid ester product is at least 80% and the biobased carbon content of the acrylic acid product is at least 40%.

25. The process of claim 24, wherein the catalyst is sulfuric acid, hydrochloric acid, phosphoric acid, trifluoroacetic anhydride, p-toluene sulphonic acid, methane sulfonic acid, silica, titanium dioxide, alumina, a clay, zinc oxide, zinc chloride, iron chloride or dibutyl tin laurate.

26. The process of claim 24, wherein the n-butanol has 0% biobased content or 100% biobased content.

27. The process of claim 24, wherein the biomass mixture is not pyrolyzed.

* * * * *